(12) United States Patent
Halldin et al.

(10) Patent No.: US 9,226,804 B2
(45) Date of Patent: Jan. 5, 2016

(54) FIXTURE AND A FIXTURE SET AND A METHOD

(75) Inventors: Anders Halldin, Mölndal (SE); Stig Hansson, Askim (SE); Johan Holmström, Kållered (SE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/444,945

(22) Filed: Apr. 12, 2012

(65) Prior Publication Data

US 2012/0264083 A1   Oct. 18, 2012

Related U.S. Application Data

(60) Provisional application No. 61/475,324, filed on Apr. 14, 2011.

(30) Foreign Application Priority Data

Apr. 14, 2011  (EP) ..................... 11162478

(51) Int. Cl.
*A61C 8/00*  (2006.01)

(52) U.S. Cl.
CPC ............ *A61C 8/0022* (2013.01); *A61C 8/0025* (2013.01)

(58) Field of Classification Search
CPC ....... A61C 8/0022; A61C 8/0025; A61C 8/00
USPC ...................... 433/201.1, 172–174
See application file for complete search history.

(56) References Cited

U.S. PATENT DOCUMENTS

| 5,588,838 | A  | * | 12/1996 | Hansson et al. | ............... | 433/173 |
| 5,823,777 | A  |   | 10/1998 | Misch et al. | | |
| 7,517,218 | B2 | * | 4/2009  | Hansson | ........................ | 433/174 |
| 7,677,891 | B2 | * | 3/2010  | Niznick | ........................ | 433/174 |
| 7,959,440 | B2 | * | 6/2011  | Hansson | ........................ | 433/174 |
| 8,029,285 | B2 | * | 10/2011 | Holmen et al. | ............... | 433/174 |
| 2004/0006346 | A1 | * | 1/2004  | Holmen et al. | ................. | 606/73 |
| 2008/0020347 | A1 | * | 1/2008  | Hansson | ........................ | 433/173 |

(Continued)

FOREIGN PATENT DOCUMENTS

| CN | 201775688 U | 3/2011 |
| DE | 102006007541 A1 * | 8/2007 |

(Continued)

OTHER PUBLICATIONS

European Search Report, Application No. 11162478.9, Search completed Jan. 17, 2012.

(Continued)

*Primary Examiner* — Cris L Rodriguez
*Assistant Examiner* — Mirayda A Aponte
(74) *Attorney, Agent, or Firm* — David A. Zdurne; Douglas J. Hura; Leana Levins

(57) ABSTRACT

The present invention relates to a fixture, such as a dental fixture, for insertion into a bore hole arranged in bone tissue, comprising a threaded leading portion and a threaded trailing portion located coronally of the leading portion. By a widened threading at the trailing portion, the bone tissue is subjected to a static strain beyond the yield strain of the bone tissue. The invention also relates to a fixture set and to a method of insertion of a fixture into a bore hole arranged in bone tissue.

25 Claims, 11 Drawing Sheets

(56) References Cited

U.S. PATENT DOCUMENTS

| | | |
|---|---|---|
| 2009/0136898 A1 | 5/2009 | Kim |
| 2010/0330534 A1* | 12/2010 | Hyun .......................... 433/174 |
| 2011/0045437 A1* | 2/2011 | Arni ............................. 433/174 |
| 2011/0070558 A1* | 3/2011 | Park et al. ................... 433/174 |
| 2011/0097688 A1* | 4/2011 | Rebaudi ....................... 433/174 |
| 2011/0195380 A1* | 8/2011 | Giorno ......................... 433/174 |
| 2012/0178048 A1* | 7/2012 | Cottrell ........................ 433/174 |

FOREIGN PATENT DOCUMENTS

| | | |
|---|---|---|
| EP | 0997112 A1 | 6/2000 |
| EP | 2233108 A1 * | 9/2010 |
| EP | 2292176 A1 | 3/2011 |
| WO | 2000003657 A1 | 1/2000 |
| WO | 03015654 A1 | 2/2003 |
| WO | WO 03015654 A1 * | 2/2003 |
| WO | 2005079697 A1 | 9/2005 |
| WO | 2009054650 A1 | 4/2009 |
| WO | 20090054005 A2 | 4/2009 |
| WO | WO 2009054650 A1 * | 4/2009 |
| WO | 20090072764 A1 | 6/2009 |

OTHER PUBLICATIONS

McCalden R.W. et al, Age-related changes in the tensile properties of cortical bone, The Lournal of Bone and Joint Surgery, vol. 75-A No. 8, Aug. 1993.

Gibson, J. Biomechanics, vol. 18, No. 5, pp. 317-328, 1985.

Kold S. et al, Compacted cansellous bone has a spring-back effect. Acta Orthopaedica Scandinavica, 2003; 74(5): 591-595.

International Search Report, Application No. PCT-EP2012-056725, Search completed Aug. 14, 2012.

Extended European Search Report, Application No. 11162478.9, Search completed Sep. 16, 2011.

* cited by examiner

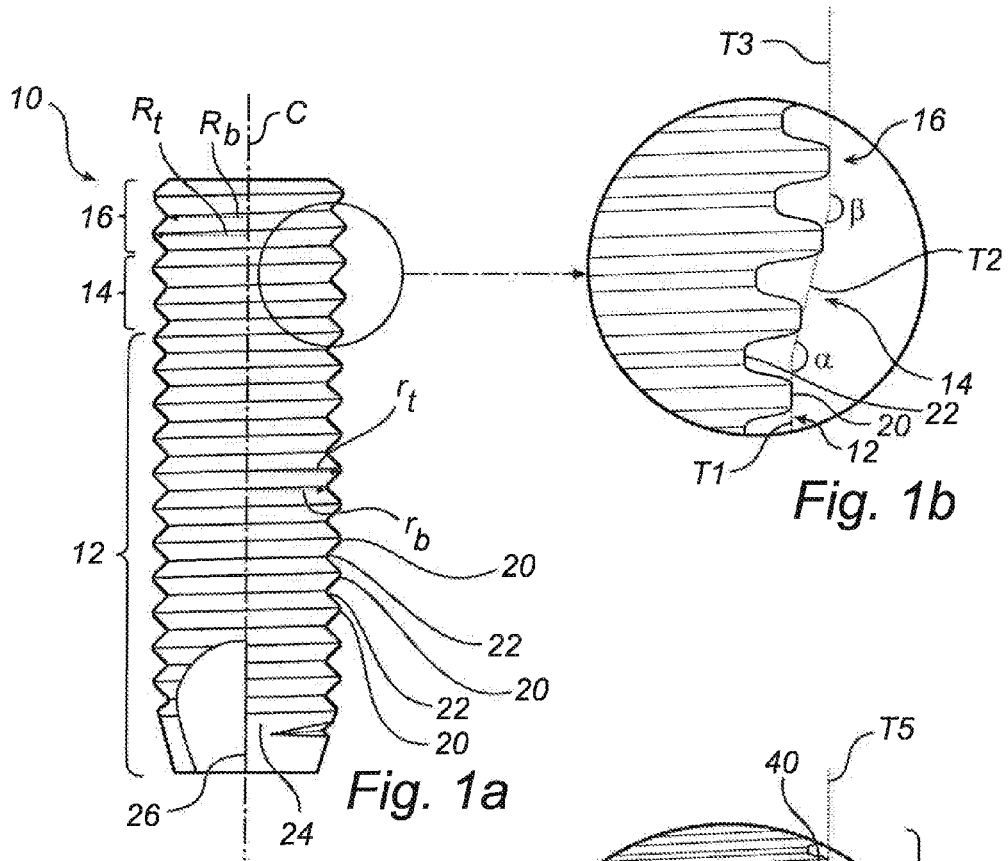
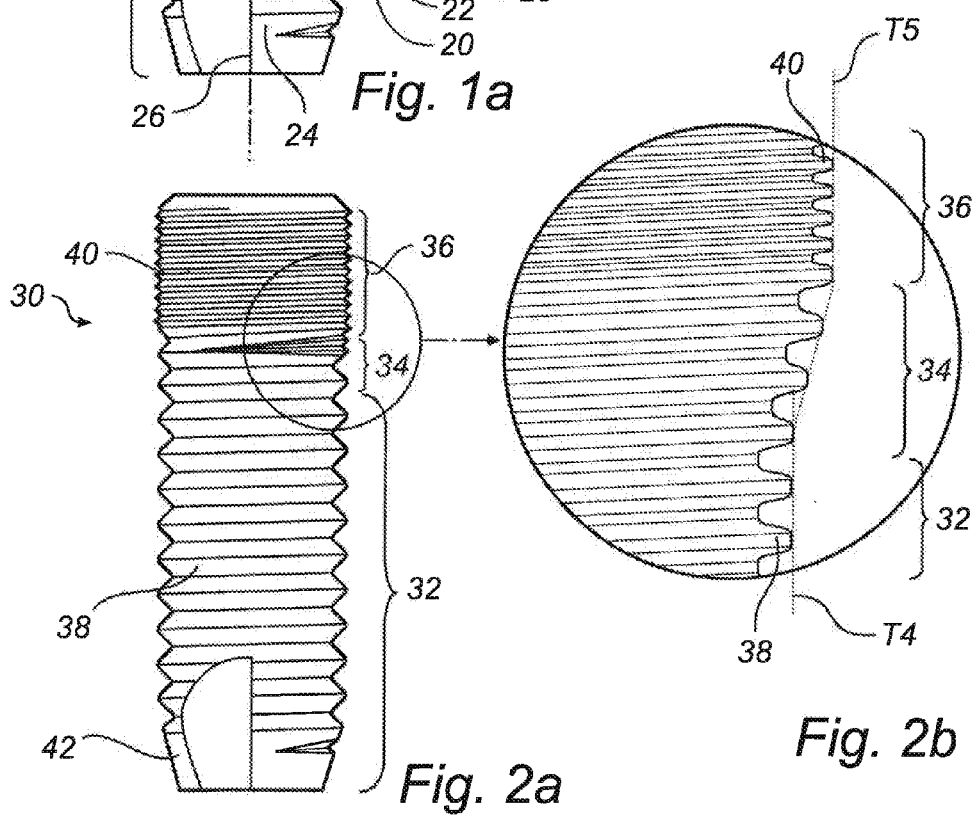

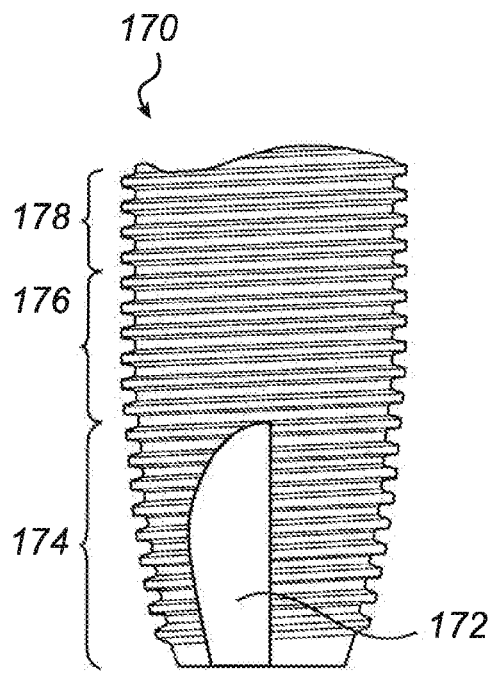
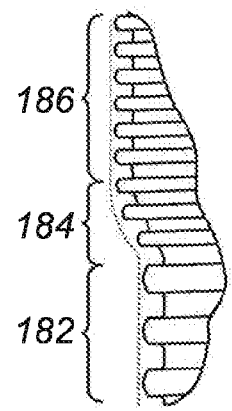
Fig. 12    Fig. 13
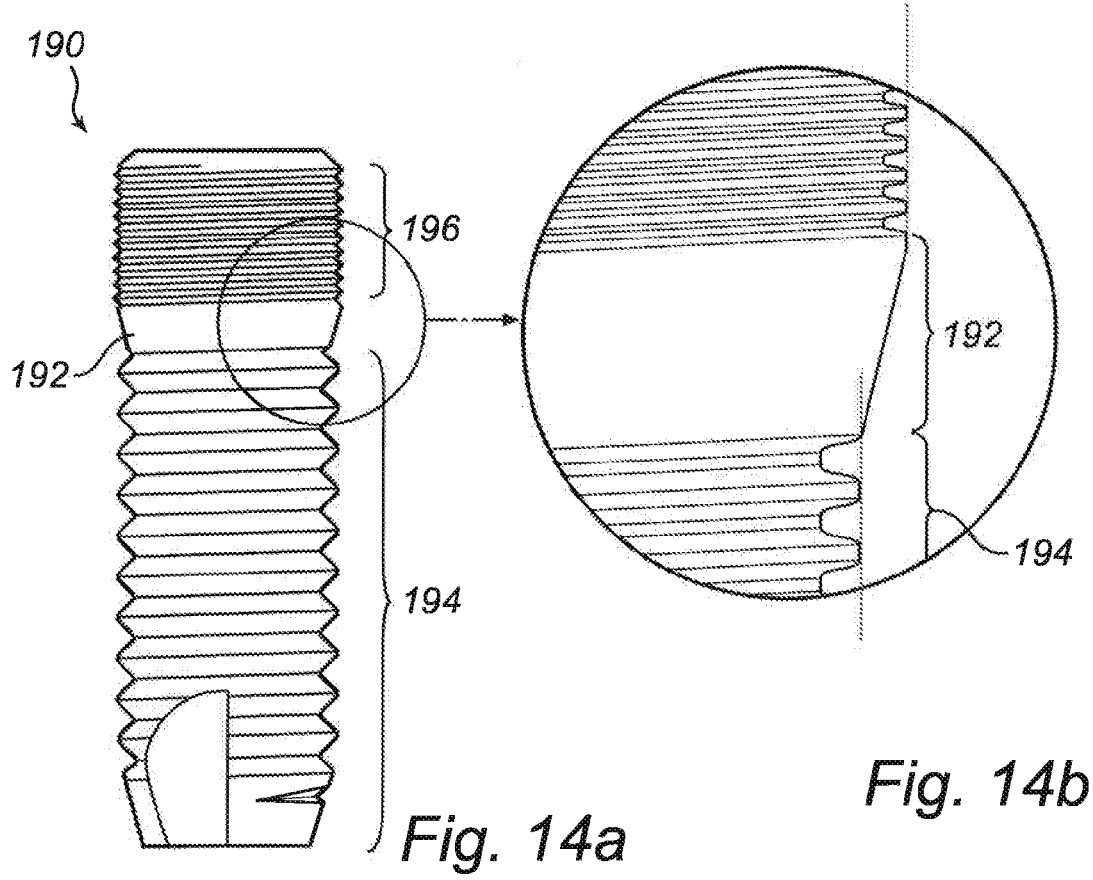
Fig. 14a    Fig. 14b

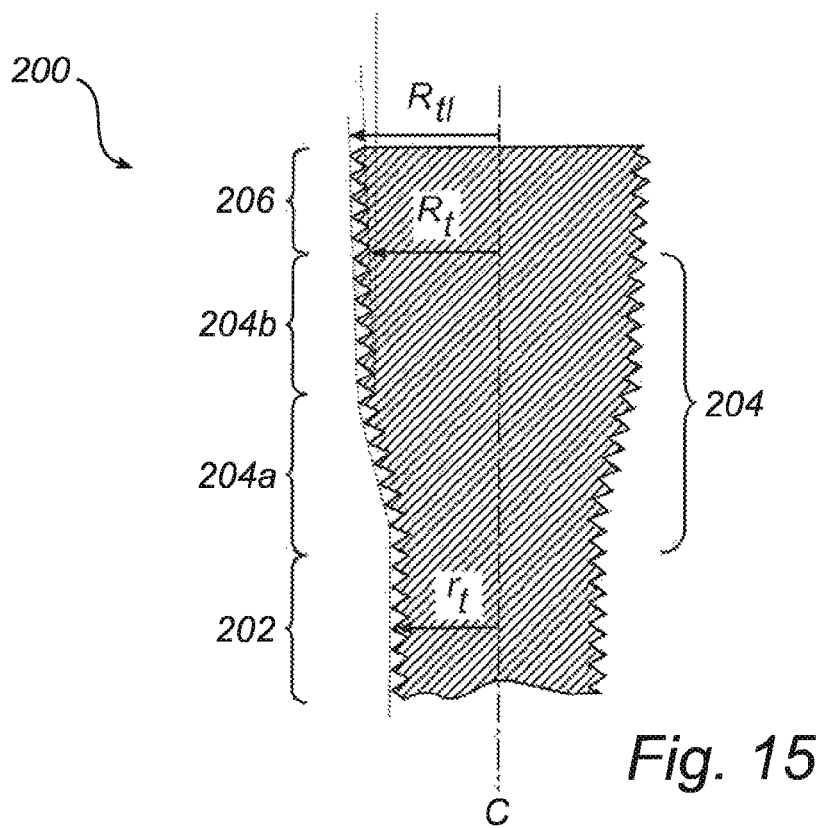
Fig. 15
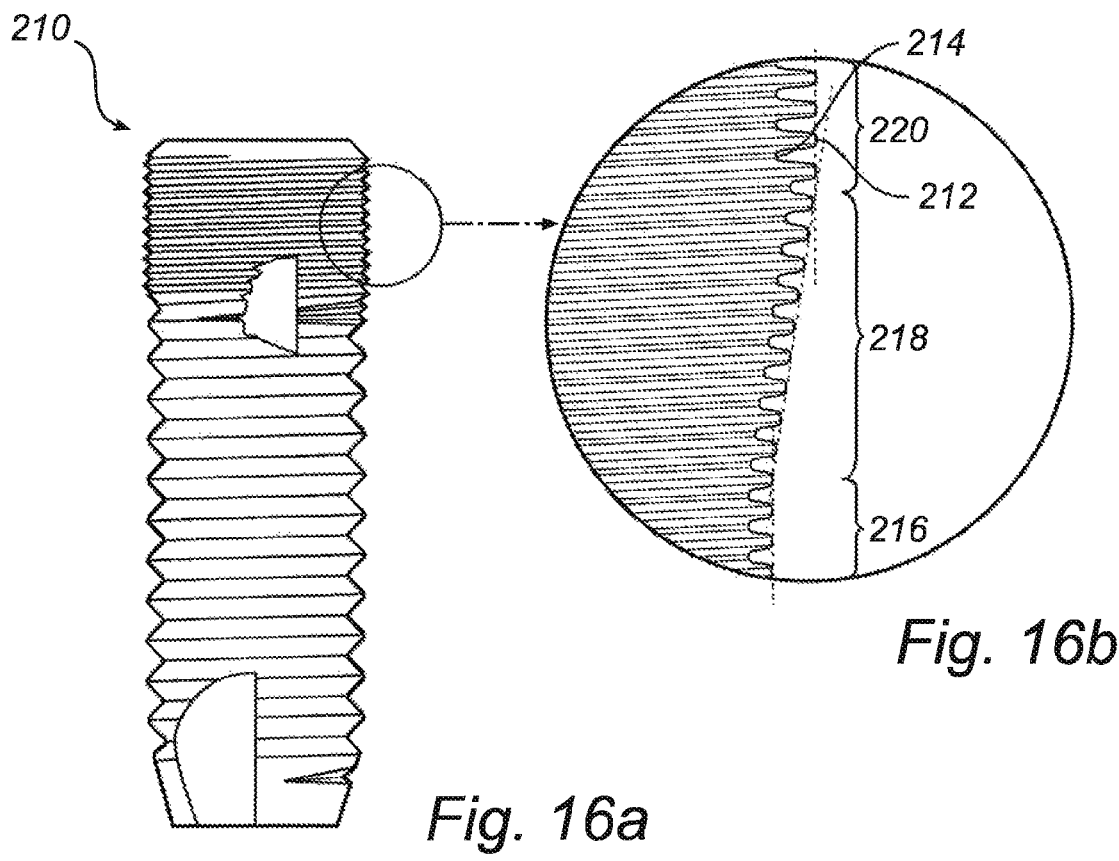
Fig. 16b
Fig. 16a

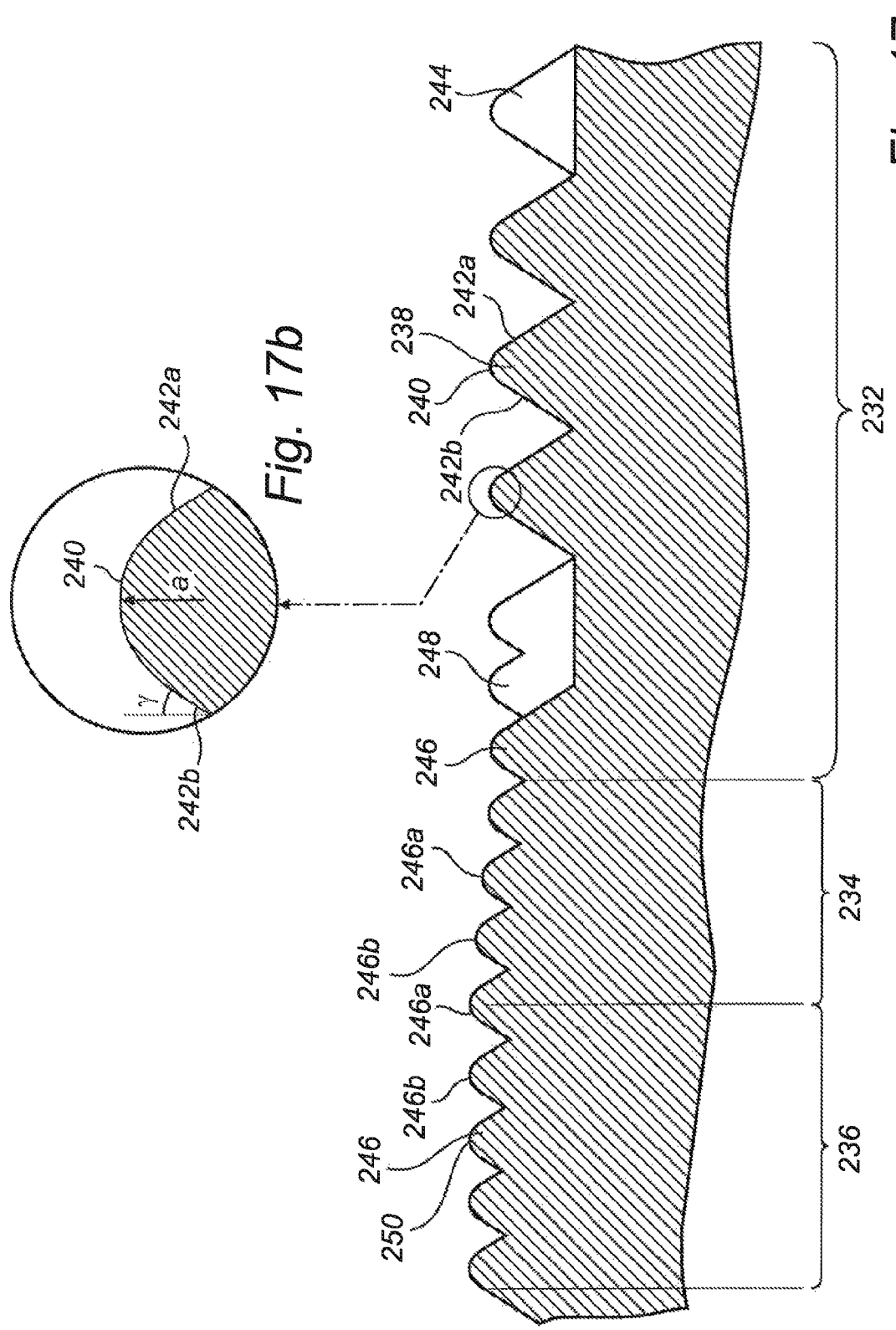

FIXTURE AND A FIXTURE SET AND A METHOD

TECHNICAL FIELD

The present invention relates to a fixture, such as a dental fixture, for insertion into a bore hole arranged in bone tissue, the fixture comprising a threaded outer surface for engagement with the bone tissue. The invention also relates to a fixture set and to a method of inserting a fixture into a bore hole arranged in bone tissue.

BACKGROUND OF THE INVENTION

A frequent way today to restore a damaged limb, such as lost tooth, is to install a fixture in the adjacent bone tissue and replace the damaged parts. In this respect, for a successful result, the fixture should become fully stable and correctly joined to the bone. The term osseointegration is used for this joining effect, the basic meaning of this term being the bone tissue growth into the fixture surface. The two major contributors to this joint are a mechanical joint and an organic joint. The former being generally influenced by the macro geometry of the bore into which the fixture is installed, and by the macro geometry of the fixture, and is a direct effect of how well these two work together. The latter one being a continuously evolving and developing effect, particularly the time immediately after installation, and being generally influenced by how well the micro surface structure of the fixture interacts with the bone tissue.

Due to ingrowth there will be an interlocking effect between the bone and the fixture. Also, the mechanical joint is developed over time since the bone tissue, under ideal conditions, may grow into surface cavities of the fixture, and grow into voids left between the fixture and the bore after installation.

During installation of a fixture into the bone tissue, the bone is subjected to both stress and strain. The relationship between stress and strain is substantially linear up to a yield point (yield strain). Up to the yield point the bone is deformed elastically. However, beyond the yield point the bone will deform plastically. In order to provide for good healing conditions and stability of the fixture in the bone, care is taken to maintain the elasticity of the bone tissue and to avoid exceeding the yield point.

There is a continuous endeavour in the industry to further increase the stability of fixtures implanted in bone tissue and to improve the basic conditions during the healing phase after fixture installation. One example is the provision of the fixture surface with different types of structures, such as micro-roughened or blasted structures for increasing the contact surface between the fixture and the bone.

Nevertheless, there is till room for further development of fixtures as regards their stability in bone tissue.

SUMMARY OF THE INVENTION

An object of the present invention is to provide a fixture, in particular a dental fixture, which has a high stability/strength during the healing phase of the fixture. This and other objects, which will become apparent in the following, are accomplished by means of a fixture defined in the accompanying claims.

The present invention is based on the insight that exceeding the yield point of the bone during and after implantation may actually be beneficial to the strength/stability of the fixture during the healing phase of the bone. In particular, the inventors have found that tensile strains in the circumferential direction which exceed the ultimate strain of the bone, i.e. when the bone cracks, may also be beneficial to trigger the biological response during the healing phase after fixture installation. Although cracks may be formed near the fixture, there will be present stabilizing surrounding bone tissue.

In this application, when strain is discussed, or when different values of strain are discussed, unless explicitly specified, the discussion may relate to tensile strain and/or compressive strain. All strain-related numbers are presented in absolute values.

Accompanying FIG. 7 is an illustration of the relationship between stress and strain in the cortical bone tissue. The yield point is at the transition between the straight part (elastic deformation zone) and curved part (plastic deformation zone) of the graph. The ultimate strain is at the other end of the curved part.

Accompanying FIG. 8 is an illustration of the relationship between stress and strain in cancellous bone tissue. For cancellous bone, the behavior up to the yield point (i.e. where the straight part of the graph transits into the curved part) substantially corresponds to that in cortical bone. However, as may be seen from FIG. 8, the behavior above the yield point differs somewhat between cancellous bone and cortical bone.

It should be noted that the graphs in FIG. 7 and FIG. 8 illustrate the absolute values of the stresses and strains.

The inventors have realized that a static strain in bone in the range of 0.01-0.3 (absolute values) provides a good bone strength during the healing phase, i.e. above the yield strain (for a normal 70 year old patient the yield strain of cortical bone may be below 0.01). In particular, the inventors have identified that the lower part of the range is suitable for cortical bone, while the upper part of the range is suitable for spongious cancellous bone.

The insertion of a fixture with a certain torque means that static strains will be induced in the surrounding bone. The magnitude of these static strains do not only depend on the insertion torque but also depend on the fixture design, the shape of the bone preparation, the bone anatomy, the bone quality and possibly also on the fixture surface topography. Rather than to elaborate on these different parameters, some of which are difficult to estimate, the inventors have ingeniously realized that it is possible to achieve an adequately controlled static strain by fixture design.

In a circular geometry, the tensile strain in the circumferential direction is given by the increase in circumference divided by the initial circumference. For instance, with an initial diameter D the circumference is $\pi \cdot D$. If the diameter is increased by $\Delta D$, then the new circumference becomes $\pi \cdot (D+\Delta D)$. Thus, the increase in circumference is $\pi \cdot (D+\Delta D) - \pi \cdot D = \pi \cdot \Delta D$. Dividing the increase in circumference with the initial circumference of $\pi \cdot D$ results in a strain $\Delta D/D$.

By providing a female thread with a first radius r in the bone tissue surrounding the bore hole (the radius being the distance from the bore hole axis to the bone thread) and by providing the fixture with a threaded portion having threads at a second radius R which is larger than the first radius r, a pressure will be applied to the bone when said threaded portion is rotated into the bone via said bone threads. The enlarged radius R will thus lead to a condensation of the bone tissue. In analogy with the above explained strain $\Delta D/D$ (and assuming that any deformation of the fixture may be neglected), the maximum strain will thus be $$\frac{R-r}{r}.$$

This means that by controlling the difference in radius between said threaded fixture portion and the bone thread with which the threads of said portion will mate, a controlled static strain may be achieved.

For instance, by having a threaded leading portion of the fixture with a first radius r corresponding to the radius of the bone threads, i.e. the distance from bore hole axis to the bone threads, and a threaded trailing portion having a second radius R which is larger than said first radius said controlled strain may be achieved.

The bone threads may be achieved either by pre-tapping with a separate tapper or by tapping means, such as cutting edges, on a self-tapping fixture.

Thus, the inventive idea may in general terms be described as providing a bore hole in the bone tissue, then providing a female thread in the bone tissue surrounding the bore hole, and then applying a static radial pressure to the cortical bone so that a strain in the range of 0.01-0.3 is achieved in the cortical bone.

According to at least a first aspect of the invention, a fixture for insertion into a bore hole arranged in bone tissue is provided. The fixture comprises a leading portion and a trailing portion, both of said portions comprising a respective outer surface being threaded for engagement with bone tissue, wherein thread tops and thread bottoms are provided alternatingly in the axial direction of the fixture, wherein the threading of the leading portion is provided with at least one cutting means/cutting edge for making a female thread in the bone tissue, wherein in the leading portion the largest radial distance from the fixture axis to a thread top of said cutting edge is $r_t$ and the largest radial distance from the fixture axis to a thread bottom of said cutting edge is $r_b$, wherein in the trailing portion the smallest radial distance from the fixture axis to a thread top is $R_t$ and the smallest radial distance from the fixture axis to a thread bottom is $R_b$, the fixture comprising an intermediate transition portion having an apical end which borders to the leading portion and a coronal end which borders to the trailing portion, wherein the transition portion has an axial length L between its apical and coronal ends, wherein at least one of the ratios $$\frac{R_t - r_t}{r_t} \text{ and } \frac{R_b - r_b}{r_b}$$

is in the range of 0.01-0.3, and wherein any coronal widening of the trailing portion, with respect to the radial distance from the fixture axis to the thread tops and/or thread bottoms, is per axial unit length smaller than at least one of the ratios $$\frac{R_t - r_t}{L} \text{ and } \frac{R_b - r_b}{L}.$$

Thus, when the cutting edges of the leading portion make a female thread in the bone there will be substantially no strain, since bone is cut away rather than pressed away. When the threaded trailing portion enters the female thread in the bone, due to the increased diameter of the trailing portion, its threads will press the bone in the radial direction creating a static strain in the bone tissue.

The transition portion is provided for achieving said increased diameter, i.e. to widen the fixture from the leading portion to the trailing portion. The transition portion may be threaded. However, alternatively, it may be non-threaded. The function of the transition portion can be regarded as to radially displace the thread tops and/or thread bottoms. With regard to thread tops the transition portion widens the fixture having said radial distance $r_t$ (fixture axis to thread top in leading portion) to having said radial distance $R_t$ (fixture axis to thread top in trailing portion). Similarly, with regard to thread bottoms the transition portion widens the fixture from having said radial distance $r_b$ (fixture axis to thread bottom in leading portion) to having said radial distance $R_b$ (fixture axis to thread bottom in trailing portion). The axial length of the transition portion is L.

It should be understood that said radial distances $r_t$ and $r_b$ defined by the thread top and thread bottom, respectively, provided with a cutting edge are present in the leading portion. Any axial section of the fixture having larger radial distances from a fixture axis to thread top/bottom than $r_t/r_b$ is instead part of the transition portion or the trailing portion.

The trailing portion may suitably be cylindrical in order to provide a foreseeable static strain to the bone. However, alternatively, the trailing portion may be slightly widening in the coronal direction in order to compensate for any grinding effect caused by the threads rotating in the bone. In case of a coronally widened trailing portion, such a widening per axial unit length should not exceed the above described widening of the transition portion. Therefore, for a coronally widened trailing portion, the radial distance from the fixture axis to a first thread top may be a first radial distance, and the radial distance from the fixture axis to a second thread top may be a second radial distance. The first and second thread tops are separated by an axial distance. When taking the difference between the second and the first radial distance, and dividing said difference with said separating axial distance, the result must not exceed $$\frac{R_t - r_t}{L}.$$

The corresponding condition applies when comparing thread bottoms in the trailing portion, i.e. their radial increase per axial unit length must not exceed $$\frac{R_b - r_b}{L}.$$

Thus, it should be understood that while the function of the transition portion is to widen the implant so as to reach a suitable strain level, the function of the trailing portion is primarily to maintain that pressure. Therefore, any widening of the trailing portion should, suitably, only compensate for grinding effects and not to further increase the strain on the bone.

According to at least one example embodiment, the transition portion comprises an outer surface being threaded for engagement with the bone tissue, wherein the outer surface of the leading portion forms an angle of less than 180° in relation to the outer surface of the transition portion, and wherein the outer surface of the transition portion forms an angle of greater than 180° in relation to the outer surface of the trailing portion.

Said forming of an angle between the outer surfaces of the different portions should be understood as an angle formed by a geometrical tangent touching the thread tops in one portion being compared with a tangent touching the thread tops in another portion, or alternatively as an angle formed by a tangent touching the thread bottoms in one portion being compared with a tangent touching the thread bottoms in another portion. For instance, a tangent touching the thread bottoms in the transition portion may form an angle of greater than 180° with respect to a tangent touching the thread bottoms in the trailing portion. It should be understood that said tangents touching the thread tops and/or thread bottoms lie in a plane which contains the central axis of the fixture.

Thus, a transition portion may be provided to achieve a diametrical increase between the leading portion and the trailing portion along the apical-coronal direction of the fixture. According to at least one example embodiment, the leading portion is substantially cylindrical. According to at least one example embodiment, the leading portion is tapering. According to at least one example embodiment, a coronal part of the leading portion is cylindrical while an apical part thereof is tapering, or vice versa. Thus, at a transversal border plane where the leading portion and the transition portion meet, the extensions of the two portions may form an angle of less than 180°, regardless of the shape of the leading portion.

According to at least one example embodiment, the leading portion and the transition portion may both be tapered, wherein the angle formed between the two portions is 180°. The coronal end of the cutting edge(s) in the leading portion may be used to define the transversal border plane where the leading portion and the transition portion meet.

It should be understood that the transition portion does not necessarily have to be conically widened in the coronal direction (i.e. conically tapered in the apical direction), but can have other alternative shapes. For instance, according to at least one example embodiment, the coronal widening of the transition portion presents a concave or convex shape.

Similarly, as mentioned previously, according to at least one example embodiment, the trailing portion is substantially cylindrical. According to at least one example embodiment, the trailing portion is tapering. According to at least one example embodiment, a coronal part of the trailing portion is cylindrical while an apical part thereof is tapering, or vice versa. Thus, at a transversal border plane where the trailing portion and the transition portion meet, the extensions of the two portions may form an angle of greater than 180°, regardless of the shape of the trailing portion.

According to at least a second aspect of the invention, a fixture for insertion into a bore hole arranged in bone tissue is provided. The fixture comprises a leading portion, a transition portion located coronally of the leading portion, and a trailing portion located coronally of both the leading portion and the transition portion, each one of said portions presenting a respective outer surface being threaded for engagement with the bone tissue, wherein thread tops and thread bottoms are provided alternatingly in the axial direction of the fixture, wherein the outer surface of the leading portion forms an angle of less than 180° in relation to the outer surface of the transition portion, and wherein the outer surface of the transition portion forms an angle of greater than 180° in relation to the outer surface of the trailing portion, wherein in the leading portion the largest radial distance from the fixture axis to a thread top is $r_t$ and the largest radial distance from the fixture axis to a thread bottom is $r_b$, wherein in the trailing portion the largest radial distance from the fixture axis to a thread top is $R_t$ and the largest radial distance from the fixture axis to a thread bottom is $R_b$, wherein at least one of the ratios $$\frac{R_t - r_t}{r_t} \text{ and } \frac{R_b - r_b}{r_b}$$

is in the range of 0.01-0.3.

Thus, according to this aspect of the invention, the leading portion does not necessarily comprise a cutting edge. On the contrary, the leading portion may lack any cutting edges. Instead a separate thread maker/tapper is used to prepare the female bone threads. However, according to at least one example embodiment of the second aspect of the invention, the leading portion may be provided with one, two, three or more cutting edges.

According to at least one example embodiment of the second aspect of the invention, the threading of the leading portion is provided with at least one cutting edge for making a female thread in the bone, wherein said largest distance $r_t$ in the leading portion is the largest radial distance from the fixture axis to a thread top of said cutting edge and said largest radial distance $r_b$ is the largest radial distance from the fixture axis to a thread bottom of said cutting edge.

According to at least one example embodiment of either one of said first and second aspects of the invention, at least one of the ratios $$\frac{R_t - r_t}{r_t} \text{ and } \frac{R_b - r_b}{r_b}$$

is in the range of 0.01-0.1, such as in the range of 0.01-0.03, suitably in the range of 0.01-0.02.

The strain range of 0.01-0.02 is normally between the yield strain and ultimate strain of human cortical bone. However, as mentioned previously, even with strains exceeding the ultimate strain of human cortical bone, beneficial effects may be accomplished. Of course, for cancellous bone, considerably higher strains may be applied to the bone, since in cancellous bone the yield strain and ultimate strain are much higher than for cortical bone. This is reflected in at least one example embodiment in which at least one of the ratios $$\frac{R_t - r_t}{r_t} \text{ and } \frac{R_b - r_b}{r_b}$$

is in the range of 0.06-0.3, suitably in the range of 0.06-0.1. While the narrower range may still be suitable for use in cortical bone, the wider range is also suitable for cancellous bone.

According to at least one example embodiment, the axial length of the threading of the trailing portion is about 0.5-4 mm, suitably 1-3 mm. Such axial length substantially corresponds to normal thickness of cortical bone. Thus, fixtures according to such an embodiment are particularly suitable for applying a static strain to the cortical bone. Therefore, suitably, the trailing portion is a coronal end portion of the bone apposition surface of the fixture.

According to at least one example embodiment, the axial length of the threading of the trailing portion is greater than 1 mm, such as greater than 3 mm, suitably greater than 4 mm.

Fixtures according to such an embodiment are suitable for cancellous bone, which is located below the cortical bone. Thus, the axial length should be large enough to reach through the cortical bone and down to the cancellous bone. Suitably, for such an installation of a fixture, the bore hole at the cortical bone may be countersunk, i.e. widened, in order to avoid too high strain provided by the trailing portion on the cortical bone. This will allow a high strain to be applied to the cancellous bone, without providing the same high strain to the cortical bone.

Suitably, in the trailing portion, not only the thread top(s) and/or thread bottom(s) having the smallest radial distance to the fixture axis are dimensioned to provide said strain ranges, but also the other thread tops and/or thread bottoms of the trailing portion are so dimensioned. This is reflected in at least one example embodiment, according to which in the trailing portion the largest radial distance from the fixture axis to a thread top is $R_{tl}$ and the largest radial distance from the fixture axis to a thread bottom is $R_{bl}$, wherein at least one of the ratios $$\frac{R_{tl} - r_t}{r_t} \text{ and } \frac{R_{bl} - r_b}{r_b}$$

is in the range of 0.01-0.3, suitably in the range of 0.01-0.1, such as in the range of 0.01-0.03, suitably in the range of 0.01-0.02.

When all the thread tops in the trailing portion are touched by a geometrical tangent which is parallel with the central axis of the fixture, then $R_{tl}$ is equal to $R_t$.

However, when $R_{tl}$ is larger than $R_t$ and the two thread tops are separated by an axial distance X, then in accordance with the previous discussions, $$\frac{R_{tl} - R_t}{X}$$

should not exceed $$\frac{R_t - r_t}{L}.$$

Although in at least one example embodiment, the fixture does not comprise any other threaded portions, in other example embodiments the fixture may, for instance, comprise one or more threaded portions, such as coronally of the trailing portion.

As mentioned previously, the trailing portion may have different alternative shapes. According to at least one example embodiment, a geometrical tangent touches substantially all of the thread tops or substantially all of the thread bottoms in the trailing portion, wherein said tangent is parallel with the fixture axis. Suitably, said tangent touches the threading of the trailing portion nearest a transversal border plane, at which the trailing portion meets the transition portion. It should be understood that said tangents touching the thread tops and/or thread bottoms lie in a plane which contains the central axis of the fixture.

Similarly, according to at least one example embodiment, a geometrical tangent touches substantially all of the thread tops or substantially all of the thread bottoms in the leading portion, wherein said tangent is substantially parallel with the fixture axis. Suitably, said tangent touches the threading of the leading portion nearest a transversal border plane, at which the leading portion meets the transition portion.

According to at least one example embodiment, the outer surface of the leading portion forms an angle of 177°-179°, such as 178° in relation to the outer surface of the transition portion.

According to at least one example embodiment, the axial length of the transition portion is about 0.5-4 mm, suitably 1-2 mm. The transition portion may entirely lack threads or may be threaded along some or all of its axial length. Therefore, according to at least one example embodiment, the axial length of the threading of the transition portion is about 0.5-4 mm, suitably 1-2 mm. Suitably, the transition portion lacks cutting edges.

In view of the just-mentioned example embodiments, assuming that the outer surface of the leading portion forms an angle of 178° in relation to the outer surface of the transition portion and that the axial length of the transition portion is 1 mm, that would result in a radial increase of 1 mm·tan (180°-178°)=0.035 mm provided by the flaring transition portion. Thus, with r being 1 mm and R being 1 mm+0.035 mm, the resulting strain would be 0.035/1=0.035.

According to at least one example embodiment, the threads in the trailing portion are microthreads. In an alternative embodiment, only parts of the threads in the trailing portion are microthreads. In yet an alternative embodiment, the threads in the trailing portion are macrothreads.

According to at least one example embodiment, at least a coronal portion of the transition portion is provided with microthreads which are continuous with microthreads in the trailing portion. In at least one alternative embodiment, the entire threading of the transition portion is in the form of microthreads. According to at least one additional or alternative example embodiment, at least a coronal portion of the leading portion is provided with microthreads, which may suitably be continuous with the microthreads in the transition and trailing portions.

According to at least one example embodiment, the trailing portion is conically widened in the coronal direction. This may be suitable in order to compensate for any grinding effect on the bone caused by the threading during insertion.

According to at least one example embodiment, the threads in the trailing portion have the same thread profile as the threads in the leading portion. Thus, in at least one example embodiment the thread profile along the threaded portions is constant. According to an alternative example embodiment, the threads in the trailing portion have a larger thread profile compared to the profile of the threads in the leading portion. A thread profile comprises two flanks, a top interconnecting said two flanks, a bottom formed between two adjacent threads, said flanks forming an angle with a plane which is perpendicular to the fixture axis and which angle lies in a plane containing the extension of the fixture axis, said profile further having a height. Said top may comprise a top radius and said bottom may comprise a bottom radius.

According to at least one example embodiment, the threads in the trailing portion have the same thread profile as the profile of the threads in the transition portion and/or the leading portion. According to at least one example embodiment, said thread profile is a microthread profile. According to at least one example embodiment, the threads in the trailing portion are microthreads having substantially the same profile as the outermost part of the threads in the transition portion and/or the leading portion.

By having a constant or substantially constant thread profile throughout the different portions, the radial pressure caused by the trailing portion can be effectively controlled. In other words, with regard to the fixture axis, the thread profile may simply be subject to parallel displacement in the radial direction when comparing the leading portion and the trailing portion.

According to at least one example embodiment, the threads in the trailing portion, the transition portion and the leading portion have the same top radius, the same apical flank angle and the same coronal flank angle. For instance, even though the threads in the leading portion may at least partially be provided with macrothreads, while the trailing portion may be provided with microthreads, thus having different thread height, because of the same top radius and flank angles, the profile/contour of the microthreads will fit the profile/contour of the female bone threads created by the macrothreads. Thereby, the bone is well supported also by the microthreads. Suitably, part of the leading portion may be provided with microthreads having a cutting edge for making female threads in the bone.

According to at least one example embodiment, said trailing portion is a first trailing portion and said transition portion is a first transition portion, the fixture further comprising a cutting portion, a second transition portion, and a second trailing portion, wherein the cutting portion has an apical end which borders to the first trailing portion and a coronal end which borders to the second transition portion, wherein the second transition portion has a coronal end which borders to the second trailing portion, wherein said cutting portion and said second trailing portion comprise a respective outer surface being threaded for engagement with bone tissue, wherein thread tops and thread bottoms are provided alternatingly in the axial direction of the fixture, wherein the threading of the cutting portion is provided with at least one cutting edge for making a female thread in the bone tissue, wherein in the cutting portion the largest radial distance from the fixture axis to a thread top of said cutting edge is $R'_t$ and the largest radial distance from the fixture axis to a thread bottom of said cutting edge is $R'_b$, wherein $R'_t \geq R_t$ and $R'_b \geq R_b$, wherein in the second trailing portion the smallest radial distance from the fixture axis to a thread top is $R''_t$ and the smallest radial distance from the fixture axis to a thread bottom is $R''_b$, wherein at least one of the ratios $$\frac{R''_t - R'_t}{R'_t} \text{ and } \frac{R''_b - R'_b}{R'_b}$$

is in the range of 0.01-0.1.

Thus, two axially separated locations of tensile strain may be provided to the bone with a fixture having along its axis an additional portion for cutting threads in the bone, and additional transition and trailing portion. Thus, the widening of the implant provided by the first transition portion enables the first trailing portion to provide a first tensile strain to the bone, while the widening of the implant provided by the second transition portion enables the second trailing portion to provide a second tensile strain to the bone. Although, said first and second tensile strains may have the same value, it may be advantageous to have different values. For instance, the fixture may be designed so that said first tensile strain will substantially be provided to the cancellous bone while the second tensile strain will be substantially provided to the cortical bone. In such case, since the ultimate strain of the cancellous bone is higher than the ultimate strain of the cortical bone, the applied first tensile strain may suitably be higher than the second applied tensile strain. In other words, $$\frac{R_t - r_t}{r_t}$$

may suitably be higher than $$\frac{R''_t - R'_t}{R'_t},$$

and/or $$\frac{R_b - r_b}{r_b}$$

may suitably be higher than $$\frac{R''_b - R'_b}{R'_b}.$$

Suitably, for the corresponding reasons as for the first trailing portion, any coronal widening of the second trailing portion, with respect to the radial distance from the fixture axis to the thread tops and/or thread bottoms, is per axial unit length smaller than at least one of the ratios $$\frac{R''_t - R'_t}{L'} \text{ and } \frac{R'' - R'_b}{L'},$$

wherein L' is the axial length of the second transition portion.

The inventive fixture, according to either one of the first and second aspects of the invention, may be applicable to different parts of the human bone tissue. According to at least one example embodiment, said fixture is a dental fixture for arrangement in jawbone.

According to at least a third aspect of the invention, there is provided a method of inserting a fixture, such as a dental fixture, into a bore hole arranged in bone tissue, comprising:
  making a female threading in a surface of the bone tissue defining the bore hole, wherein thread tops and thread bottoms are provided alternatingly in the axial direction of the bore hole, wherein the largest radial distance from the bore hole axis to a thread top is $r_t$ and the largest radial distance from the bore hole axis to a thread bottom is $r_b$,
  inserting a threaded condensation portion of a fixture into the bore hole, such that at least one thread spiral follows in the path created by said female threading, wherein in said condensation portion the smallest radial distance from the fixture axis to a thread top is $R_t$ and the smallest radial distance from the fixture axis to a thread bottom is $R_b$, wherein at least one of the ratios $$\frac{R_t - r_t}{r_t} \text{ and } \frac{R_b - r_b}{r_b}$$

is in the range of 0.01-0.3.

It should be understood that, in this application, the thread tops and thread bottoms of the female threading have the same point of reference as thread tops and thread bottoms of the fixture. In other words, a thread top is located at a larger radial distance from the fixture axis and bore hole axis, respectively, than an adjacent thread bottom.

The female bone thread may either be achieved by a separate thread maker, e.g. a separate tapper. Alternatively, the female bone thread may be provided by a cutting portion on the fixture, said cutting portion being arranged apically of the condensation portion.

The condensation portion has the same function as the above described trailing portion, i.e. it has the function to apply a radial pressure onto the bone tissue. Thus, the method according to the third aspect of the invention, may be performed with a fixture having a leading portion, an optional transition portion, and a trailing portion as described above. Furthermore, the method according to the third aspect may incorporate any embodiments and/or features discussed above in connection with the first or second aspects of the invention.

According to a fourth aspect of the invention, a fixture set is provided. The fixture set comprises:
a fixture comprising a condensation portion,
a thread maker provided with at least one cutting edge and adapted to be rotated into a bore hole arranged in bone tissue for making a bone thread in the bone tissue prior to insertion of said fixture, the thread maker comprising a threaded outer surface, wherein thread tops and thread bottoms are provided alternatingly in the axial direction of the thread maker, wherein the largest radial distance from the thread maker axis to a thread top of said cutting edge is $r_t$ and the largest radial distance from the thread maker axis to a thread bottom of said cutting edge is $r_b$, wherein the fixture comprises an outer surface being threaded for engagement with bone tissue, wherein thread tops and thread bottoms are provided alternatingly in the axial direction of the fixture, wherein the smallest radial distance from the fixture axis to a thread top of said condensation portion is $R_t$ and the smallest radial distance from the fixture axis to a thread bottom of said condensation portion is $R_b$,
wherein at least one of the ratios $$\frac{R_t - r_t}{r_t} \text{ and } \frac{R_b - r_b}{r_b}$$

is in the range of 0.01-0.3.

According to at least one example embodiment, the fixture in said fixture set is a fixture having one or more of the features discussed in connection with the first and second aspects of the invention.

The fixture discussed in the various aspects and embodiments of the invention, may be a dental fixture comprised in a dental implant. A dental implant may, in addition to the dental fixture, also comprise a superstructure, such as an abutment.

The dental fixture is for use as the anchoring member of a dental prosthesis. To this end, the dental fixture is insertable into a pre-prepared bore hole in the bone tissue of a jawbone (maxilla or mandible) at a site where the dental prosthesis is required. The dental fixture is normally rotated into the bore hole.

The dental fixture is a screw-type dental fixture. To this end the bore hole may be provided with internal (female) threads, in advance or may be left un-tapped with the dental fixture provided with a self-tapping capacity, e.g. by the provision of one or more axially-extending cutting recesses, edges or notches, etc in the fixture thread. For instance, an apical end portion of the fixture may be provided with 2-4 cutting recesses, such as 3 cutting recesses. Other number of cutting recesses are readily conceivable.

A superstructure for connecting a prosthetic part to the fixture may comprise an abutment, spacer or other transmucosal component which engages to the dental fixture to bridge the gingiva overlying the maxilla or mandible. The prosthetic part, e.g. a crown, bridge or denture may be secured to the abutment. There are various other forms that the superstructure can take. For instance, the prosthetic part may be secured directly to the dental fixture. A dental implant may thus comprise an abutment connected to the dental fixture, or the dental fixture without an abutment.

The term "coronal" is here and throughout this application used to indicate a direction towards a head end or trailing end of the dental implant. For instance, in a situation where an abutment is connected to a dental fixture, the coronal direction of the abutment would be a direction towards the part of the abutment being directed away from the fixture. Conversely, the term "apical" indicates a direction towards an insertion or leading end of the component. Thus, apical and coronal are opposite directions. Furthermore, the terms "axial", "axial direction" or "axially" are used throughout this application to indicate a direction taken from the coronal end to the apical end, or vice versa. The terms "radial", "radial direction" or "radially" indicate a direction perpendicular to the axial direction.

A blind bore or socket may extend apically into the fixture body from the coronal end to an end surface in-between the apical and coronal ends of the fixture body for a superstructure to be secured to the fixture. The socket may comprise an internally-threaded section for screw connection of the superstructure to the fixture. A rotational lock for the superstructure may be provided in the socket, such as an internal polygonal side wall, e.g. hexagonal, or alternatively one or more protrusions from or indentations in the wall of the socket. A section of the socket, such as the coronal section, may be tapered towards the apical end. The tapered section is suitably arranged coronally of the internally-threaded section.

The fixture may be used in a one stage procedure or a two stage procedure. In a one stage procedure a healing or temporary abutment is connected to the fixture to form the gingival tissue, and after a healing period the healing or temporary abutment is replaced by a permanent abutment. For a two stage procedure the fixture is provided with a cover screw and the gingival tissue is sutured over the fixture and cover screw, and after a healing period the tissue is opened up and an abutment is connected to the fixture after removal of the cover screw.

A conceivable alternative to having an abutment connected to the fixture is to have a one-piece implant, wherein a portion of the implant is embedded in bone tissue, while another portion of the implant extends from the bone tissue across the gingiva.

The fixture may have a conically tapering end portion which tapers towards the coronal end. The axial extent of this coronal end portion is small compared to the total length of the fixture, as an example no more than 4% of the total length, such as in the range of 1.5%-3.7%. The coronal end portion may suitably be provided without a threaded surface, e.g. having a smooth or a roughened (such as blasted) surface.

The fixture may have a substantially flat coronal end surface which is perpendicular to the longitudinal axis of the fixture. Alternatively, the coronal end surface may have a sloped contour relative to the longitudinal axis of the fixture, e.g. such that when positioned within the jawbone the length of the fixture is larger on a lingual side and shorter on a buccal side of the fixture. Another alternative is a saddle-shaped or wave-like coronal end surface.

The length of the dental fixture may be in the range of 5-19 mm, depending on the clinical situation. The outer diameter of the dental fixture may suitably be in the range of 2-6 mm, such as 3-5 mm.

The fixture may be substantially cylindrical or slightly tapering from the coronal end towards the apical end. If the fixture has a slight tapering, the core of the fixture and the outer periphery defined by e.g. thread tops may have the same or different angle of taper. Furthermore, the core of the fixture may be cylindrical while the thread tops describe a conicity or, conversely, the core of the fixture may be tapered while the thread tops describe a generally cylindrical geometry. Alternatively, the fixture may comprise a combination of one or more cylindrical and/or one or more tapering portions. Thus, one or more portions of the fixture may have e.g. thread tops lying in a common imaginary cylindrical surface, which cylindrical surface is parallel with the longitudinal axis of the fixture. Alternatively or additionally, one or more portions of the fixture may have thread tops lying in an imaginary conical surface which in the apical direction is tapering towards the longitudinal axis.

The externally threaded fixture may comprise one or more thread spirals.

The term "pitch" is used to indicate the axial distance between adjacent tops of a threading. The term "lead" is used to indicate the distance advanced parallel to the longitudinal axis when the fixture is turned one revolution, i.e. it corresponds to the pitch multiplied with the number of thread spirals. For a single thread spiral having a constant pitch, the lead is equal to the pitch; for a double thread spiral, the lead is twice the pitch.

The term "microthread" is used to indicate a thread having a height which is no greater than 0.2 mm. According to at least one example embodiment, the fixture is provided with microthreads having a height in the range of 0.02-0.2 mm, such as 0.05-0.015 mm, for instance 0.1 mm. The term "macrothread" is used to indicate a thread having a height which is greater than 0.2 mm. According to at least one example embodiment, the fixture is provided with macrothreads having a height in the range of 0.25-0.35 mm, such as 0.3 mm.

Suitably, microthreads may be located coronally of macrothreads. For instance, microthreads may be arranged to engage dense cortical bone and macrothreads may be arranged to engage porous spongious/cancellous bone. The lead of a microthread suitably corresponds to the lead of a macrothread. The macrothread pitch may, as an example, be 2-4 times, such as 3 times, the pitch of the microthreads. The pitch (top-to-top spacing) at a fixture portion provided with microthreads may be around 0.10-0.30 mm, for instance 0.20-0.24 mm. The pitch (top-to-top spacing) at a fixture portion provided with macrothreads may be around 0.30-0.90 mm, for instance 0.60-0.72 mm.

Microthreads can be regarded as defined, oriented roughness. A non-oriented roughness having smaller dimensions, for instance obtained by blasting, etching, etc., may be superimposed on microthreads as well as on macrothreads.

A thread profile may comprise two flanks, a top interconnecting said two flanks, a bottom formed between two adjacent threads, said flanks forming an acute angle v with a plane which is perpendicular to the fixture axis and which angle v lies in a plane containing the extension of the fixture axis, said profile further having a height D. The top may be curved and may have a top radius. Suitably, for $10°≤v<35°$, the top radius is greater than $0.4×D$ and, for $35°≤v<55°$, the top radius is greater than $0.2×D$.

According to at least one exemplary embodiment, the flanks of the threads have a straight extension.

According to at least one exemplary embodiment, the flanks of the threads have a curved extension. It is for example conceivable with flanks having a concave curvature. It is also conceivable with flanks having a convex curvature.

It should be understood that the basic idea of providing a controllable strain to the bone, can in all aspects of the invention, be achieved either by changing the radial distance from fixture axis to the thread tops or by changing the radial distance from fixture axis to the thread bottoms, or by changing both of said radial distances. This means that, for instance, the first aspect of the invention encompasses the following definition:

A fixture for insertion into a bore hole arranged in bone tissue, comprising a leading portion and a trailing portion, both of said portions comprising a respective outer surface being threaded for engagement with bone tissue, wherein thread tops and thread bottoms are provided alternatingly in the axial direction of the fixture, wherein the threading of the leading portion is provided with at least one cutting edge for making a female thread in the bone tissue, wherein in the leading portion the largest radial distance from the fixture axis to a thread top of said cutting edge is $r_t$ and the largest radial distance from the fixture axis to a thread bottom of said cutting edge is $r_b$, wherein in the trailing portion the smallest radial distance from the fixture axis to a thread top is $R_t$ and the smallest radial distance from the fixture axis to a thread bottom is $R_b$, the fixture comprising an intermediate transition portion having an apical end which borders to the leading portion and a coronal end which borders to the trailing portion, wherein the transition portion has an axial length L between its apical and coronal ends, wherein $$\frac{R_t - r_t}{r_t}$$

is in the range of 0.01-0.1, and wherein any coronal widening of the trailing portion, with respect to the radial distance from the fixture axis to the thread tops, is per axial unit length smaller than the ratio $$\frac{R_t - r_t}{L}.$$

Similarly, the first aspect of the invention encompasses a corresponding definition of thread bottoms with regard to the ratios $$\frac{R_b - r_b}{r_b} \text{ and } \frac{R_b - r_b}{L}.$$

BRIEF DESCRIPTION OF THE DRAWINGS

FIG. 1a illustrate a fixture according to at least one example embodiment of the invention.

FIG. 1b illustrates a fixture according to at least one other example embodiment of the invention.

FIG. 2a illustrates a fixture according to at least one other example embodiment of the invention.

FIG. 2b illustrates a fixture according to at least one other example embodiment of the invention.

FIG. 12 illustrates a detail of a fixture according to at least one example embodiment of the invention.

FIG. 13 illustrates a detail of a fixture according to at least one example embodiment of the invention.

FIG. 14a illustrates a fixture according to yet another example embodiment of the invention.

FIG. 14b illustrates a fixture according to yet another example embodiment of the invention.

FIG. 15 illustrates schematically a fixture according to at least one example embodiment of the invention.

FIG. 16a illustrates a fixture according to at least one further example embodiment of the invention.

FIG. 16b illustrates a fixture according to at least one further example embodiment of the invention.

FIG. 17a illustrates a detail of a fixture according to at least one example embodiment of the invention.

FIG. 17b illustrates a detail of a fixture according to at least one example embodiment of the invention.

DETAILED DESCRIPTION OF THE DRAWINGS

Figures 3A, 3B:
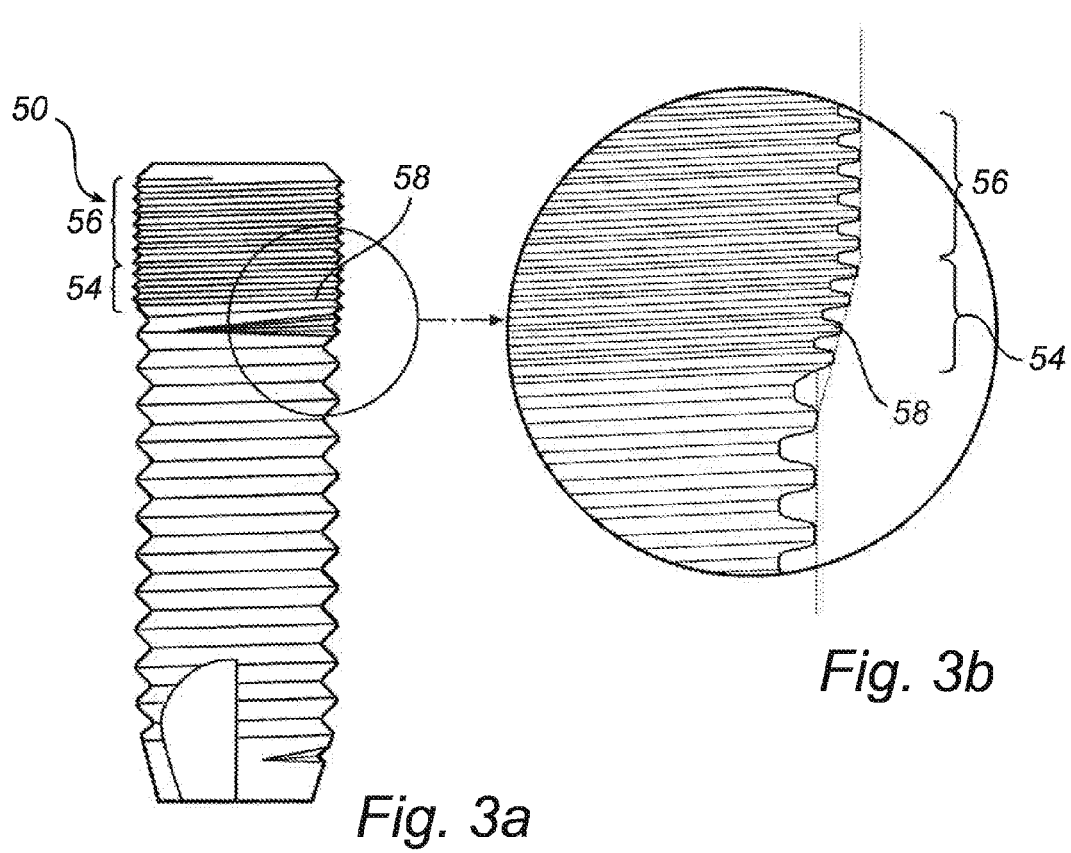
FIG. 3a illustrates a fixture according to at least a further example embodiment of the invention.
FIG. 3b illustrates a fixture according to at least a further example embodiment of the invention.

FIG. 1a is a side view illustrating a fixture 10 according to at least one example embodiment of the invention. FIG. 1b is an enlarged view of a detail of FIG. 1a.

The fixture 10 in FIGS. 1a and 1b comprises a leading portion 12, a transition portion 14 (see in particular FIG. 1b) located coronally of the leading portion, and a trailing portion 16 located coronally of both the leading portion 12 and the transition portion 14. Each one of said portions present a respective outer surface being threaded for engagement with the bone tissue, wherein thread tops 20 and thread bottoms 22 are provided alternatingly in the axial direction of the fixture 10.

In the illustrated example, the thread profile is constant along the length of the fixture 10. The outer surface of the leading portion 12 forms an angle α of less than 180° in relation to the outer surface of the transition portion 14, and wherein the outer surface of the transition portion 14 forms an angle β of greater than 180° in relation to the outer surface of the trailing portion 16. Since the thread profile is unchanged between the different threaded portions, both the thread tops 20 and the thread bottoms 22 of the fixture 10 can be regarded as forming the angular relationship of said outer surfaces.

For instance, as illustrated in FIG. 1b, a first tangent T1 touching the thread tops of the leading portion 12 and a second tangent T2 touching the thread tops of the transition portion 14 forms the angle α of less than 180°. Because of the unchanged thread profile, also the tangents (not shown) touching the bottoms of the leading and transition portions, respectively, form the same angle α of less than 180°. Similarly, a third tangent T3 touching the tops of the trailing portion 16 forms the angle β of greater than 180° with respect to said second tangent T2.

In the illustrated example, the leading portion 12 of the fixture 10 is substantially cylindrical, i.e. said first tangent T1 extends substantially in parallel with the central fixture axis C. In the leading portion, the radial distance from the fixture axis C to a thread top is $r_t$ and the radial distance from the fixture axis C to a thread bottom is $r_b$.

Furthermore, in the illustrated example, the trailing portion 16 is also substantially cylindrical, i.e. said third tangent T3 extends substantially in parallel with the central fixture axis. In the trailing portion the radial distance from the fixture axis to a thread top is $R_t$ and the radial distance from the fixture axis to a thread bottom is $R_b$. Since the thread profile is unchanged, the thread profile has merely made a radial parallel displacement with regard to the central axis when going from the leading portion 12 to the trailing portion 16. In other words the increase is the same with regard to the radial distance to the thread bottoms 22, i.e. the increase from $r_b$ to $R_b$, as the increase with regard to the radial distance to the thread tops 20, i.e. the increase from $r_t$ to $R_t$. Therefore, the ratio $$\frac{R_t - r_t}{r_t}$$

as well as the ratio $$\frac{R_b - r_b}{r_b}$$

is in the range of 0.01-0.3.

For instance, $r_t$ may be 2 mm and $R_t$ may be 2.1 mm, which would result in a ratio of 0.05.

Although, FIG. 1 illustrates that an apical portion 24 of the leading portion 12 is slightly tapering in the apical direction and is provided with one or more cutting edges 26, other alternatives are also conceivable, e.g. a tapering or non-tapering apical portion without cutting edges.

FIGS. 2a-2b illustrate a fixture 30 according to at least one other example embodiment of the invention. While the threading in FIGS. 1a-1b had a constant thread profile along the different portions, the threading in FIGS. 2a-2b has a varying thread profile.

Thus, in the example illustrated in FIGS. 2a-2b, the leading portion 32 is provided with a first thread profile, for instance created by a macrothread 38. The transition portion 34 also has said first thread profile. However, the transition portion 34 is conically widened away from the leading portion 32. Finally, the trailing portion 36 has a second thread profile, for instance created by a microthread 40.

In this example, the thread tops and thread bottoms of both the leading portion 32 and the trailing portion 36 are touched by respective tangents T4, T5 which are parallel to the central fixture axis. An alternative would be to have a longer part of the leading portion 32 tapering, not just the apical portion 42 of the leading portion 32. For instance, the entire leading portion 32 could be tapering and the cutting edge would extend axially along the entire tapered leading portion. The trailing portion 36 could also be slightly tapering to compensate for any grinding effect. Furthermore, the thread profile of the transition portion 34 could be another, differing from both the thread profile of the leading portion 32 and also from the thread profile of the trailing portion 36.

Although FIGS. 2a-2b illustrate a certain geometry of the thread tops of the macrothreads 38 and the microthreads 40, other geometries are conceivable. For instance, the macrothreads may have thread tops which have the same radius of curvature as the thread tops of the microthreads, e.g. as illustrated in FIGS. 17a-17b. In other example embodiments they may have different radii of curvature.

FIGS. 3a-3b illustrate a fixture 50 according to at least a further example embodiment of the invention. This example resembles to that of FIGS. 2a-2b. However, in this case, the transition portion 54 comprises a threading (e.g. microthreads 58) corresponding to the threading of trailing portion 56. Thus, the transition portion 54 has said second thread profile.

In the examples illustrated in FIGS. 2a-2b and FIGS. 3a-3b, the microthreading has two thread spirals while the macrothreading has one thread spiral. While the individual thread spirals in the microthreads have the same lead as the single thread spiral of the macrothreads, the distance (i.e. the pitch) between adjacent microthread tops is half of the distance between adjacent macrothread tops. One of the microthread spirals will follow the path of the macrothread spiral. The radial distance from the fixture axis to a top or bottom of said only one microthread spiral is $R_t$ or $R_b$, respectively, and the radial distance from the fixture axis to a top or bottom of the macrothread spiral is $r_t$ or $r_b$, respectively. At least one of the ratios $$\frac{R_t - r_t}{r_t} \text{ and } \frac{R_b - r_b}{r_b}$$

is in the range of 0.01-0.3.

Because the microthreads have a smaller depth than the macrothreads the above two ratios will be different. However, both ratios could very well be within said range, which would be the case if, for instance, $R_t$=3.0 mm, $R_b$=2.96 mm, $r_t$=2.92 mm and $r_b$=2.7 mm.

Figures 4, 5:
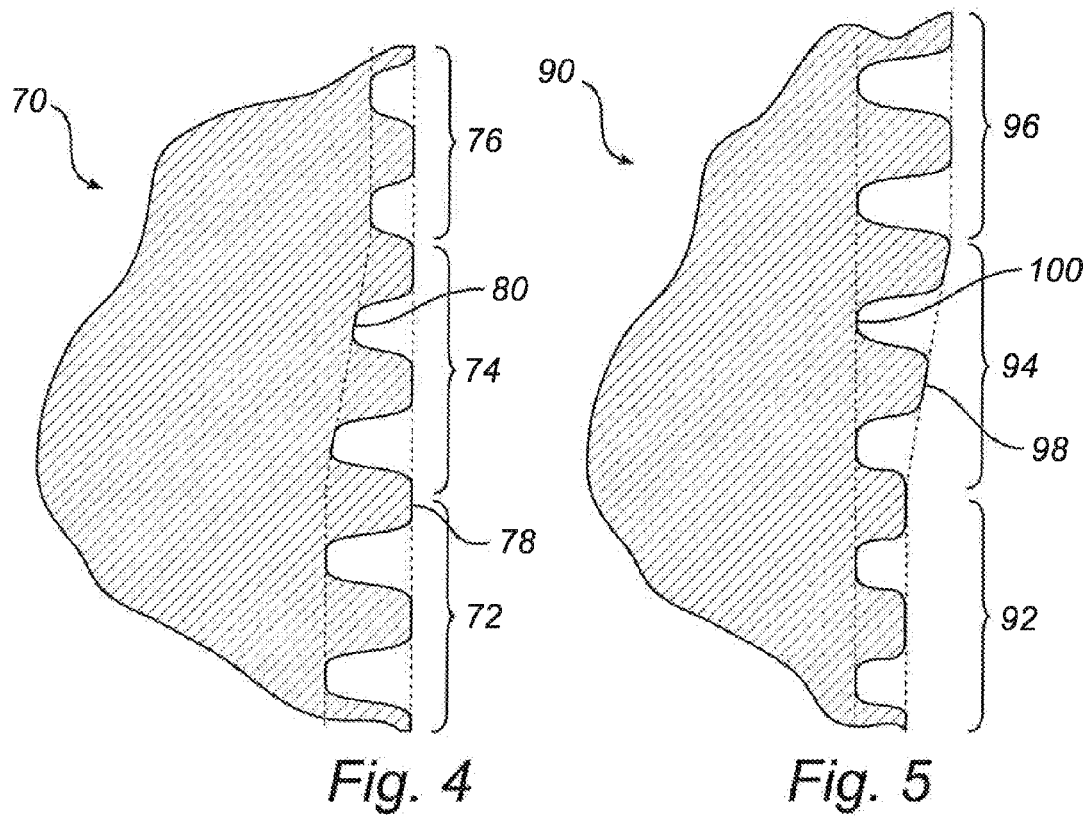
FIG. 4 illustrates in cross-section a detail of a fixture according to at least one example embodiment of the invention.
FIG. 5 illustrates in cross-section a detail of a fixture according to at least one other example embodiment of the invention.

FIG. 4 illustrates in cross-section a detail of a fixture 70 according to at least one example embodiment of the invention. In this example, going from the leading portion 72 (via the transition portion 74) to the trailing portion 76, the radial distance from the fixture axis to the thread tops 78 is constant. However, the outer surface formed by the thread bottoms 80 is changing throughout the different portions. Thus, the outer surface of the transition portion 74 formed by the thread bottoms 80 is conically widened away from that of the leading portion 72. In terms of the previously discussed radial distances, $R_t$=$r_t$, while $R_b$>$r_b$, wherein $$\frac{R_b - r_b}{r_b}$$

is in the range of 0.01-0.3. Thus, only the thread bottoms 80 provide said radial pressure to cause the desired static strain on the bone tissue.

FIG. 5 illustrates in cross-section a detail of a fixture 90 according to at least one other example embodiment of the invention. In this example, going from the leading portion 92 (via the transition portion 94) to the trailing portion 96, the radial distance from the fixture axis to the thread bottoms 100 is constant. However, the outer surface formed by the thread tops 98 is changing throughout the different portions. Thus, the outer surface of the transition portion 94 formed by the thread tops 98 is conically widened away from that of the leading portion 92. In terms of the previously discussed radial distances, $R_b$=$r_b$, while $R_t$>$r_t$, wherein $$\frac{R_t - r_t}{r_t}$$

is in the range of 0.01-0.3. Thus, only the thread tops 98 provide said radial pressure to cause the desired static strain on the bone tissue.

Figures 6A, 6B:
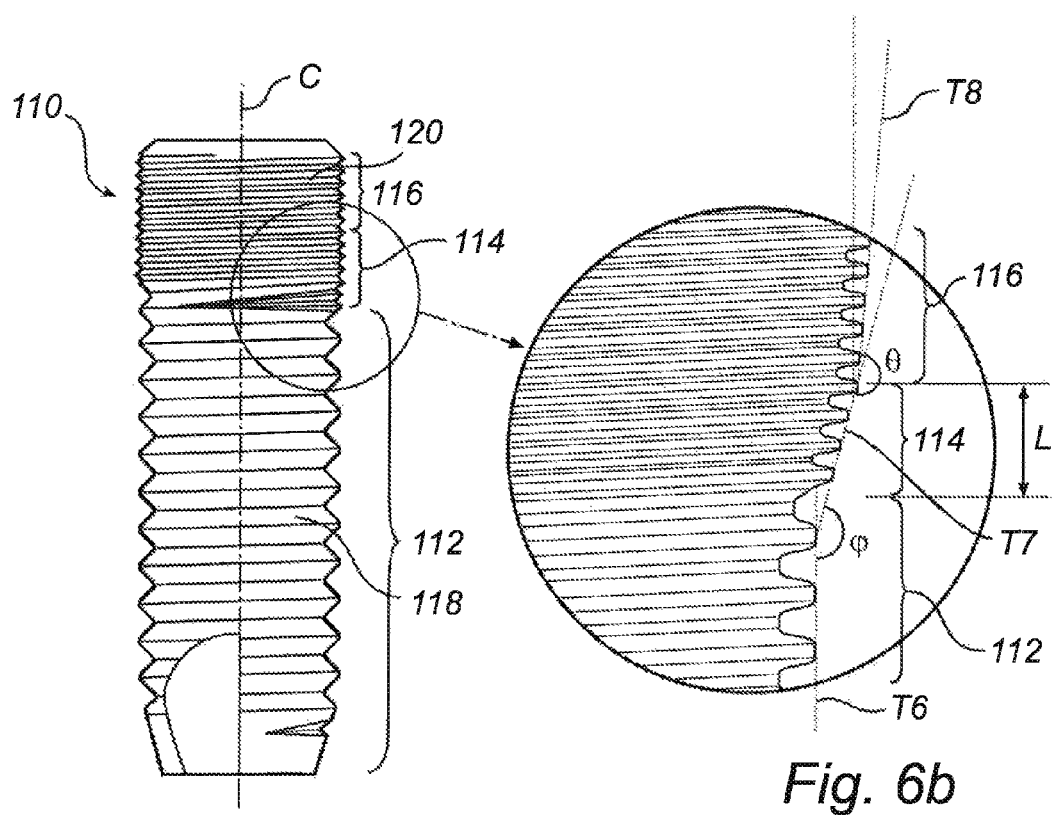
FIG. 6a illustrates a fixture according to at least yet another example embodiment of the invention.
FIG. 6b illustrates a fixture according to at least yet another example embodiment of the invention.

FIGS. 6a-6b illustrate a fixture 110 according to at least yet another example embodiment of the invention. This example is similar to that illustrated in FIGS. 3a-3b. However, in FIGS. 6a-6b, the outer surface of the trailing portion 116 is slightly angled relative to the central fixture axis C, in order to compensate for any grinding effect on the bone tissue. Thus, a first tangent T6 touching the thread tops of the leading portion 112 and a second tangent T7 touching the thread tops of the transition portion 114 form an angle φ of less than 180°. Similarly, a third tangent T8 touching the thread tops of the trailing portion 116 form an angle θ of greater than 180° with respect to said second tangent T7. However, contrary to the fixtures illustrated in, for instance, FIGS. 1a-3b, the first tangent T6 and the third tangent T8 are not parallel with each other. For the example illustrated in FIGS. 6a-6b, also a tangent (not shown) touching the thread bottoms of the trailing portion 116 is angled with respect to the fixture axis C. Thus, in FIGS. 6a-6b, both the transition portion 114 and the trailing portion 116 are conically widened in the coronal direction, the widening being greater for the transition portion 114.

The transition portion 114 has an axial length L between its apical end (bordering to the leading portion 112) and its coronal end (bordering to the trailing portion 116). Thus, the coronal widening of the trailing portion, with respect to the radial distance from the fixture axis C to the thread tops and/or thread bottoms, is per unit axial length smaller than at least one of the ratios $$\frac{R_t - r_t}{L} \text{ and } \frac{R_b - r_b}{L}.$$

It should be noted that although FIGS. 6a-6b have been illustrated with macrothreads 118 in the leading portion 112 and microthreads 120 in the trailing portion 116, the conically widened trailing portion 116 may be present in alternative embodiments as well. For instance, a single type of thread having an unchanged thread profile could be present on the fixture on the leading portion 112, the conically widened transition portion 114 and the conically widened trailing portion 116.

Figure 7:
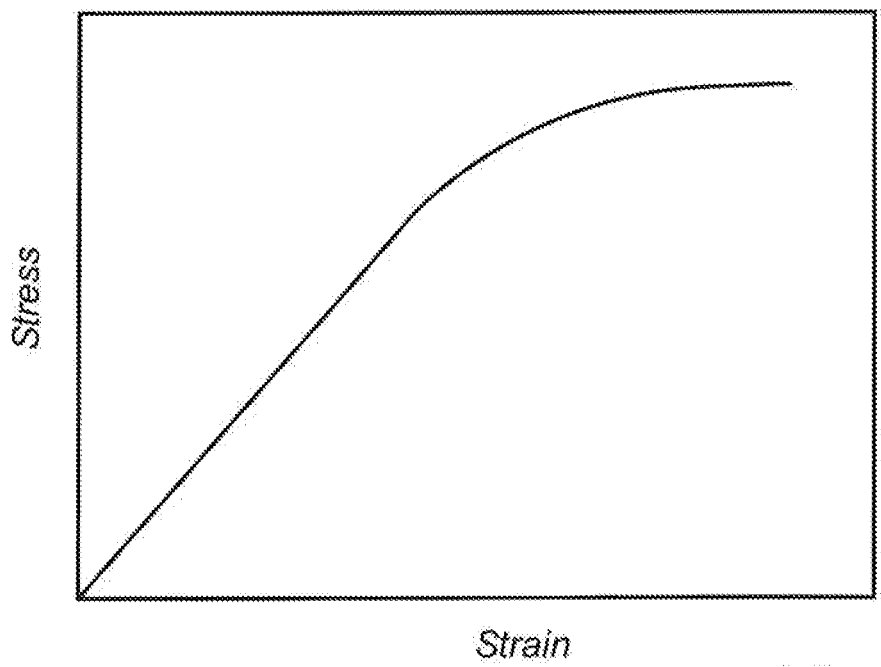
FIG. 7 is a graph illustrating a stress/strain relationship for cortical bone.

FIG. 7 is a graph illustrating a stress/strain relationship for cortical bone. In an article by McCalden R. W. et al. the relationship between ultimate strain and age is presented (McCalden R. W. et al., *Age-related changes in the tensile properties of cortical bone*, The Journal of Bone and Joint Surgery, Vol. 75-A. No. 8, August 1993). From the article, one learns that the ultimate strain is substantially linearly dependent on the person's age. For instance, an 80 year old person has in cortical bone an ultimate strain of about 0.015, a 50 year old person has an ultimate strain of about 0.025, while a 20 year old person has an ultimate strain of about 0.035. For cortical bone the yield strain is about half the ultimate strain. For instance, with reference to FIG. 7, in a 20 year old person, for a strain up to about 0.018, the stress/strain relationship could be linear and represents an elastic deformation of the bone. The interval between 0.018 and 0.035 is non-linear and represents a plastic deformation of the cortical bone. Similarly, for an 80 year old person, a strain up to 0.008 would correspond to the linear relationship and the interval between 0.008 and 0.015 would correspond to the non-linear relationship in FIG. 7.

EXAMPLE

Screw shaped fixtures, manufactured from commercially pure titanium, grade 4, were used. In order to reduce a possible grinding effect during insertion the fixtures had a turned surface. The endosseous part of the fixtures comprised three different portions; one leading (cutting) portion, one transition portion with a gradual increase in diameter and one trailing (condensation) portion. The bone bed was drilled to a final burr diameter of 3.3 mm corresponding to the core diameter ($2r_b$) of the cutting portion of the fixture. When the fixture was inserted the cutting features created a cavity in the bone which was congruent with the fixture shape of the cutting portion. When the transition portion entered the bone it created a gradual increase in the strains in the surrounding bone without cuffing. When finally the condensation portion entered the bone the predetermined bone condensation was obtained. The fixtures were installed with a standardized rotation speed of 20 revolutions/minute. Two types of test fixtures were used; one where the increase in diameter was 0.15 mm (referred to as "Group 0.15") and another with a diameter increase of 0.05 mm (referred to as "Group 0.05"). The control fixtures had no diameter increase.

The fixtures were inserted in tibia of rabbits. Test fixtures were always inserted in the left leg and control fixtures in the right leg. Group 0.15 fixtures were installed proximally in the proximal tibia metaphysis. Group 0.05 fixtures were installed distally in the proximal tibia metaphysis.

After 3.5 weeks, all fixtures were subjected to removal torque (RTQ) tests. The peak RTQ was investigated with a computerized control RTQ device, in which the values were transmitted at a frequency of 100 per second to the computer via a control box.

The fixture head was connected to the instrument, and an increasing reverse torque was applied to all the fixtures until failure of the bone-fixture interface occurred. The first peak values of resistance to reverse torque rotation were recorded in Ncm.

Prior to the animal experiment a 2D axisymmetric finite element model of the trailing portion of the fixture and the surrounding bone was developed. The fixture and the bone were modeled in a CAD software Pro/Engineer (PTC Corporate Needham, Mass. USA) and then transferred into the finite element software ANSYS 12.01 (ANSYS, Inc. Canonsburg, Pa., USA). The strain in the bone was induced by radial displacement of the fixture surface by 0.025 mm and 0.075 mm simulating a diameter increase of 0.05 mm and 0.15 mm respectively. The simulated maximum principal strain in the surrounding bone for Group 0.15 fixtures was ~0.045 (0.15 mm divided by 3.3 mm=0.045). For group 0.05 fixtures the maximum principal strain obtained was ~0.015 (0.05 mm divided by 3.3 mm=0.015).

In all sites the removal torque of the test fixtures was higher than that of the corresponding control fixtures. See Table 1.

TABLE 1

| Removal | Comparison between removal torque for test fixtures and control fixtures. | |
|---|---|---|
| | Average torque Test Ncm (Std) | Average torque Control Ncm (Std) |
| Tibia proximal (Group 0.15) | 26.0 (6.89) | 16.8 (7.83) |
| Tibia distal (Group 0.05) | 23.0 (5.31) | 17.2 (5.29) |

Strain in cortical bone from rabbits has been measured by Shunmugasamy V. C. et al. and presented in an article (Shunmugasamy V. C. et al., *High strain rate response of rabbit femur bones*. Journal of Biomechanics, 2010; 43: 3044-3050). The ultimate strain of rabbit cortical bone was measured to be about 0.02.

In the present study the fixtures were just supported by cortical bone. It should be noted that the Group 0.15 fixtures gave rise to strains (0.045) which exceeded the ultimate strain (~0.02) of cortical rabbit bone. In spite of this there was no evidence of reduced removal torque. On the contrary the removal torque of the experimental fixtures was higher than that of the control fixtures which were designed not to produce static strains in the bone. It is striking that the very highest removal torque was obtained for Group 0.15 fixtures for which the strains induced by far exceeded the ultimate strains. From the values in Table 1, one can simply calculate that for Group 0.15 fixtures the removal torque was increased by 55%, and for Group 0.05 fixtures the removal torque was increased by 34%. Obviously, the stresses in the bone, which were induced during fixture insertion, are maintained for a considerable time.

This study indicates that an increased strain provides better initial fixture stability, it is also noticeable that increased strain provides a better stability after 3.5 weeks.

In the above-mentioned article by McCalden R. W one learns that the ultimate strain is substantially linearly dependent on the person's age. The above discussed ultimate strain (~0.02 of rabbits) can be seen for a 70 year old person. While the rabbit experiments in the above discussed example showed a successful result for a strain of 0.045, which by far exceeds the ultimate strain of cortical rabbit bone (2¼ times the ultimate strain of cortical rabbit bone), and also exceeds the ultimate strain of cortical bone of a 70 year old human, it is anticipated that an even higher strain would be successful in a younger person's cortical bone. For a 20 year old person, it would correspond to applying a strain of about 0.08 (2¼ times the ultimate strain 0.035 of a 20 year old person). For a child or adolescent the ultimate strain is even higher, for instance 0.04, which means that a strain of 0.09 could be applied. The rabbit study in the above example did not measure the upper limit for suitable static radial strain, but since the Group 0.15 fixtures surprisingly provided an even better result than the 0.05 fixture, it is reasonable to assume that even higher strains relative to the ultimate strain may be suitable for cortical bone.

While the above study analyzed the strain in cortical bone, an analogy may be made to strains in cancellous bone. Thus, similarly to the previous explanations with regard to providing a tensile strain in cortical bone above the yield strain, a beneficial biological response may also be triggered by providing a tensile strain in cancellous bone above the yield strain of the cancellous bone.

Figure 8:
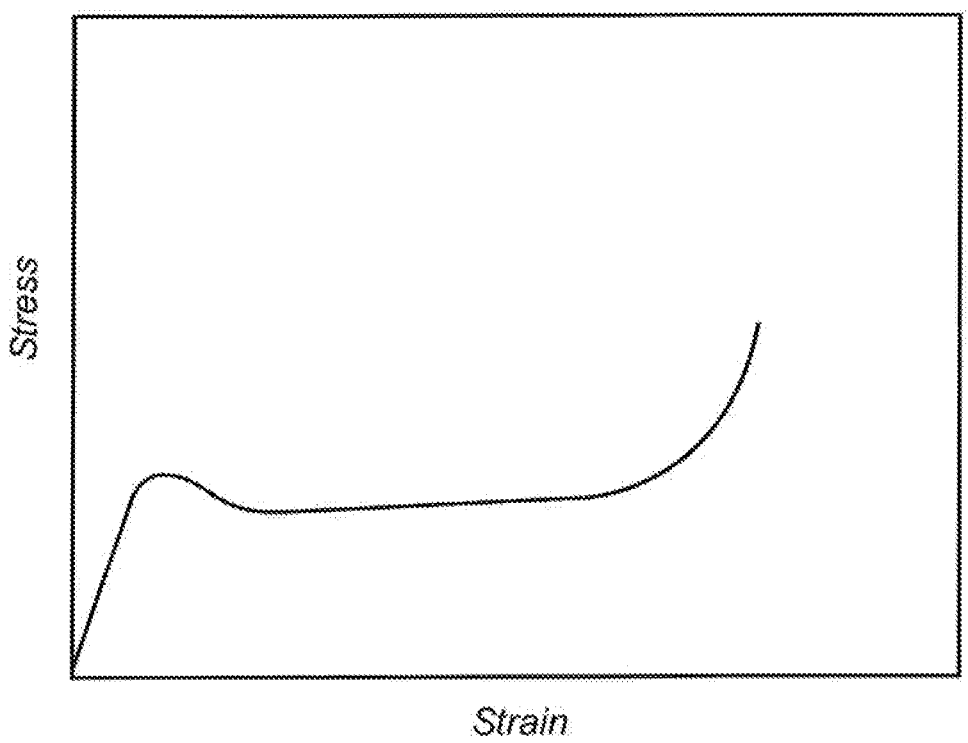
FIG. 8 is a graph illustrating a stress/strain relationship for cancellous bone.

FIG. 8 is a graph illustrating a stress/strain relationship for cancellous bone. The behavior of the graph up to the yield point is similar to that of FIG. 7, i.e. a linear relationship is presented. However, the curved part above the yield point is different and more stretched. According to Gibson, the yield strain is about 0.06 for cancellous bone (Gibson, J. Biomechanics, Vol. 18, No. 5, pp 317-328, 1985). Drawing conclusions from an article by Kold S. et al. (Kold S. et al., *Compacted cancellous bone has a spring-back* effect. Acta Orthopaedica Scandinavica, 2003; 74(5): 591-595) the yield strain for cancellous bone may be even higher. According to Kold S. et al. a bore hole of 5.0 mm in diameter was made in cancellous bone. The bone was then compacted by expanding the bore to 5.6 mm, after which the bone sprung back. During the compaction, the tensile strain $\Delta D/D$ on the cancellous bone was therefore 0.6/5=0.12. Thus, the yield strain in cancellous bone is multiple that of the yield strain in cortical bone. In addition, the plastic deformation of cancellous bone is much more stretched than for cortical bone. Thus, since a strain level of 0.1 is considered by the inventors to be suitable for cortical bone tissue, at least for some age groups, a strain level of 0.3 should be suitable for cancellous bone tissue.

Figure 9:
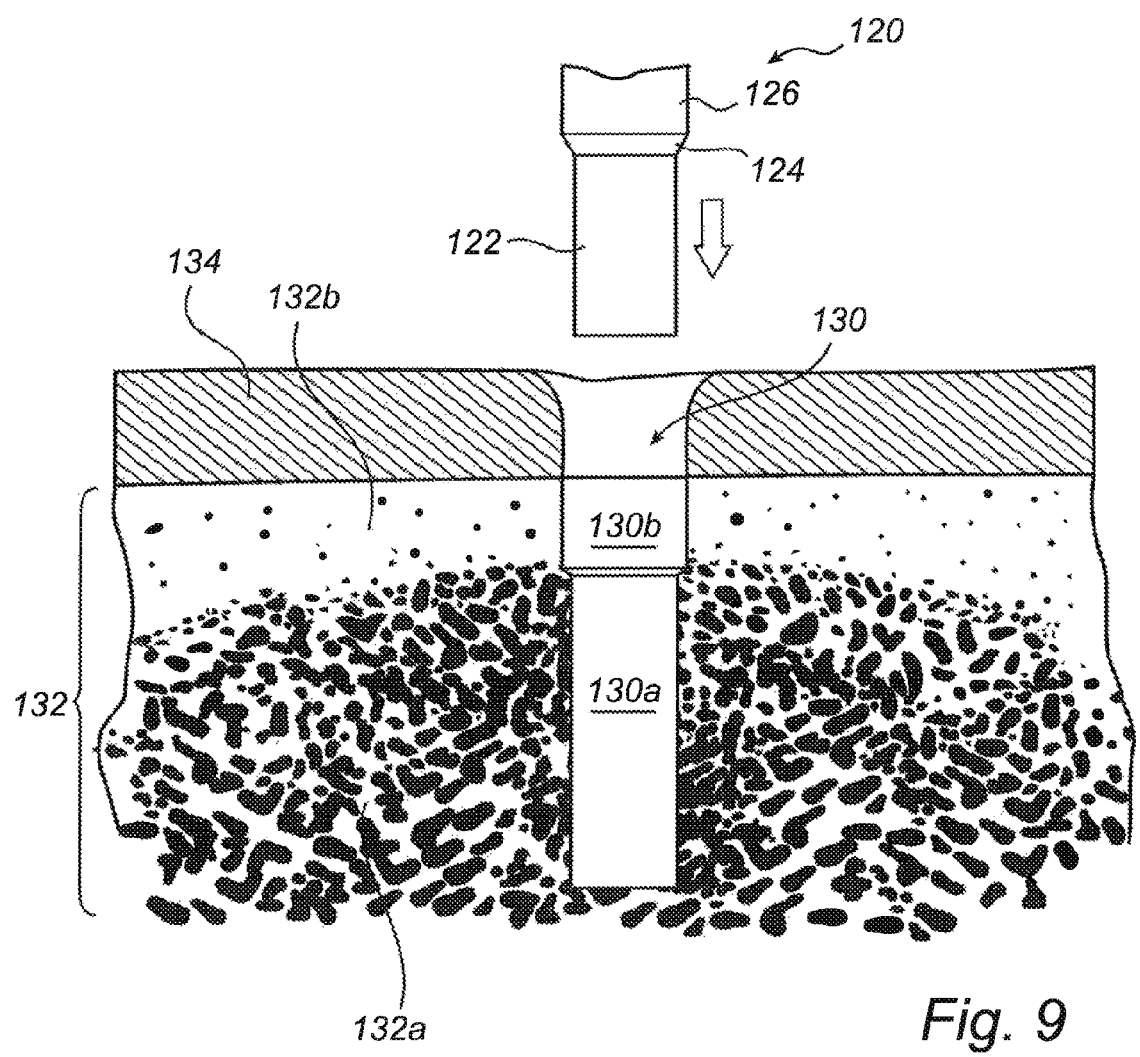
FIG. 9 illustrates an example of an installation of a fixture according to at least one example embodiment of the invention.

FIG. 9 illustrates an example of an installation of a dental fixture 120 according to at least one example embodiment of the invention. The fixture 120 is schematically illustrated as having a leading portion 122, a transition portion 124 and a trailing portion 126. The fixture 120 is intended to be installed in a bore hole 130 in the jawbone 132 under the gingiva 134. The fixture is intended to provide a strain of 0.01-0.3, suitably 0.06-0.3, such as 0.1-0.3 to the cancellous bone 132a which is located beneath the cortical bone 132b. Surrounded by cancellous bone 132a an apical section 130a of the bore hole 130 has a first diameter, e.g. substantially corresponding to the core diameter of the leading portion 122. Surrounded by cortical bone 132b a coronal section 130b of the bore hole 130 has a second, larger diameter. The larger diameter of the bore hole may, for instance, correspond to the core diameter of the trailing portion 126. Thus, because the apical section of the trailing portion 126 will be located in the cancellous bone 132a, a pressure causing the desired strain will be applied to the cancellous bone 132a. Because the bore hole 130 is countersunk in the cortical bone 132b to provide said second, larger diameter, the trailing portion 126 will not provide said pressure to the cortical bone tissue 130b.

Figure 10:
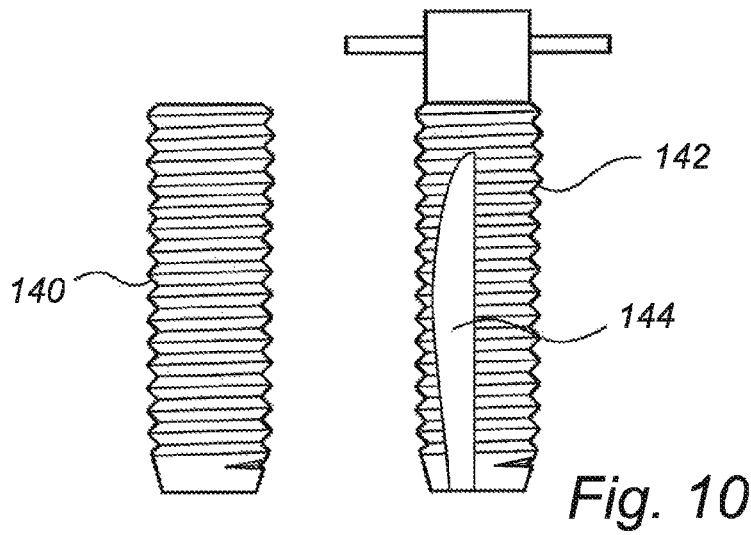
FIG. 10 illustrates a fixture arrangement, comprising a fixture and a separate tapper, in accordance with at least one example embodiment of the invention.

FIG. 10 illustrates a fixture arrangement or fixture set, comprising a fixture 140 and a separate thread maker or tapper 142, in accordance with at least one example embodiment of the invention. The fixture 140 is herein illustrated as the fixture in FIG. 1a, however, without any cutting edges. Instead the separate tapper 142, having a shape and threads with the same lead and pitch as the threads of an apical portion of the fixture 140, is provided with one or more cutting edges 144. Thus, in use, after a bore hole has been made in the jawbone, the tapper 142 is screwed into the bone, whereby the cutting edges 144 cut into the bone to make female bone threads. When the tapper 142 has been unscrewed from the bore hole the fixture 140 may be rotated into the bore hole as the female bone threads provide a path for the fixture threads to follow. When a condensation portion of the fixture, having larger radial dimension than the apical portion of the fixture, enters the bore, a strain is provided to the bone. Although the fixture in FIG. 1a has been used as the basis for the example in FIG. 10a (the apical portion corresponding to the leading portion, and the condensation portion corresponding to the trailing portion), it should be noted that the same principle applies also to other fixtures. For instance, the fixtures which have been illustrated in the other figures could be modified by omitting the cutting features, and instead use a separate tapper having cutting features to provide a matching female bone thread.

Figures 11A, 11B:
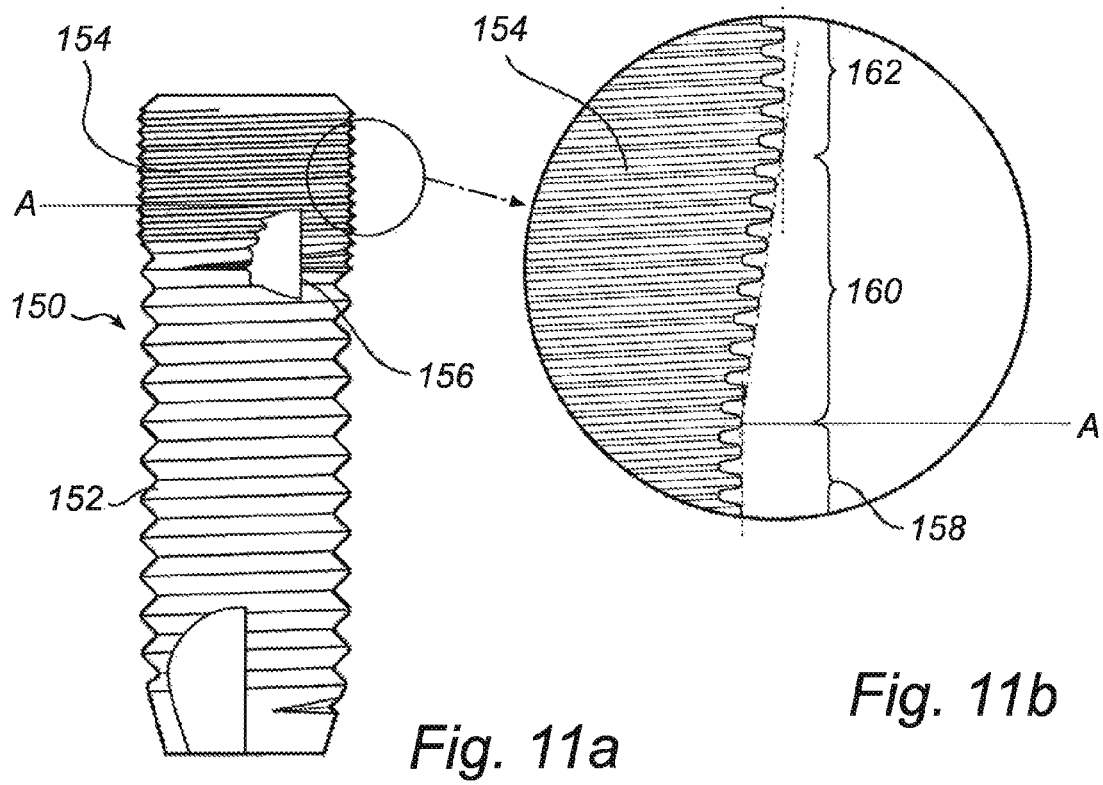
FIG. 11a illustrates a fixture according to at least one other example embodiment of the invention.
FIG. 11b illustrates a fixture according to at least one other example embodiment of the invention.

FIGS. 11a-11b illustrate a fixture 150 according to at least one other example embodiment of the invention. Similarly to the fixtures in FIGS. 2a-2b, 3a-3b and 6a-6b, the present fixture 150 comprises macrothreads 152 followed coronally by microthreads 154. As can be seen in FIG. 11a, one or more cutting edges 156 is provided at the microthreads 154 in order to cut female microthreads into the bone. As can be seen in FIG. 11b the leading portion 158 of the fixture 150 extends to an axial level A at the coronal end of said cutting edge 156 at the microthreads 154. The leading portion 158 is followed coronally by a flaring transition portion 160, which in turn is followed coronally by a substantially straight trailing portion 162. Thus, the leading portion 158, transition portion 160 and the trailing portion 162 all comprise microthreads 154 and may all have the same thread profile. Although, FIG. 11b shows substantially straight leading and trailing portions, it should be understood that in alternative embodiments they could be slightly angled, as described elsewhere in this specification.

FIG. 12 illustrates a detail of a fixture 170 according to at least one example embodiment of the invention. As mentioned previously, the leading portion does not have to be straight. For instance, the leading portion and the transition portion may be tapering with the same angle with respect to the central fixture axis. In such case the coronal end of the cutting edge(s) may define the border between the leading portion and the transition portion. This is exemplified in FIG. 12, in which the fixture 170 is widened coronally from its apical end and above the cutting edge 172. The leading portion 174 is provided with the cutting edge 172 to make a female thread in the bone. The transition portion 176 which is located just above the cutting edge 172 widens the radial distance (thread top/bottom to central fixture axis) compared to the cut radial distance in the bone (female bone thread top/bottom to centre of bore hole). The widening causes a pressure being applied to the bone, and the following trailing portion 178 is dimensioned to provide a substantially static strain within the desired range.

FIG. 13 illustrates a detail of a fixture according to at least one example embodiment of the invention. Although the transition portion may suitably be widened linearly at a certain angle with respect to the central fixture axis, other alternatives are also conceivable. For instance, as illustrated in FIG. 13 the transition portion 184 is in the form of a convex widening of the fixture from the leading portion 182 to the trailing portion 186. Another alternative would be a concave widening of the fixture. Other shapes (curved, stepped, etc.) of the transition portion are also conceivable as long as it makes the fixture wider when going from the leading portion to the trailing portion. The word "wider" should be understood as the thread tops and/or the thread bottoms have been radially displaced away from the central axis, when comparing their location at the trailing portion with their location at the leading portion.

FIGS. 14a-14b illustrate a fixture 190 according to yet another example embodiment of the invention. FIGS. 14a-14b are intended to illustrate that the transition portion 192 does not necessarily have to be threaded, but can comprise or consist of an unthreaded section of the fixture 190. Although the leading portion 194 is here illustrated as having macrothreads and the trailing portion 196 as having microthreads, it should be understood that an unthreaded transition portion can be provided in-between other leading and trailing portion configurations as well. In any case, the threads in the trailing portion may suitably be synchronized with the threads in the leading portion so that when the fixture is installed in the bone the threads in the trailing portion will follow a desired path in the bone, despite being preceded by the unthreaded transition portion.

FIG. 15 illustrates schematically a fixture 200 according to at least one example embodiment of the invention. In this fixture 200 a straight leading portion 202 is illustrated, which is coronally followed by an apical section 204a of a transition portion 204 and then a coronal section 204b of a transition portion 204. The apical section 204a of the transition portion 204 has a larger angle with respect to the central axis C than the coronal section 204b of the transition portion 204. In order to compensate for any grinding effects, the trailing portion 206 has the same angle of taper as the coronal section 204b of the transition portion 204. In the leading portion 202 the radial distance from the centre axis C to the thread top is $r_t$. The trailing portion 206 starts where the radial distance from the centre axis C to a thread top is $R_t$, wherein $$\frac{R_t - r_t}{r_t} = 0.01\text{-}0.3.$$

Thus, again it is illustrated that a transition portion may be configured in different manners, as long as the fixture is widened when going from the leading portion to the trailing portion so that a strain of 0.01-0.3 is obtained.

As shown in FIG. 15, the trailing portion 206 is conically widened. Suitably, also the largest radial distance $R_{tl}$ may fulfill the condition $$\frac{R_{tl} - r_t}{r_t} = 0.01\text{-}0.03.$$

FIGS. 16a-16b illustrate a fixture 210 according to a further example embodiment of the invention. This fixture 210 is similar to the fixture shown in FIGS. 11a-11b. However, as may be seen in FIG. 16b, while the radial distance from fixture axis to thread tops 212 is increased when going from leading portion 216 to trailing portion 220 via the transition portion 218, there are thread bottoms 214 in the trailing portion 220 which are provided at a radial distance to the fixture axis which is shorter than the radial distance of some of the transition portion thread bottoms to the fixture axis. Thus, while the thread tops 212 in the trailing portion 220 will provide the desired strain to the bone, the extra deep thread bottoms 214 in the trailing portion 220 will provide blood chambers, which may act to stimulate the re-growth of bone tissue.

FIGS. 17a-17b illustrate a detail of a fixture according to at least one example embodiment of the invention. In particular a part of the fixture is shown in cross-section, wherein the fixture has a leading portion 232, a coronally widening transition portion 234 and a substantially straight trailing portion 236. The leading portion 232 is provided with macrothreads 238 having thread tops 240 with a certain radius of curvature a. The thread tops 240 are flanked by apical and coronal flank portions 242a, 242b at a certain acute angle γ relative to a plane perpendicular to the central fixture axis. The angle γ lies in the plane containing the fixture axis. In this case the apical and coronal flanks 242a, 242b are illustrated as having the same angle γ. However, in alternative embodiments the coronal and apical flank angles may differ from each other. The macrothread 238 is provided with a cutting feature, such as a cutting edge 244, to make a corresponding female macrothread in the bone tissue.

Coronally of the macrothreads 238, the leading portion 232 is also provided with double-spiraled microthreads 246 which continue into the transition portion 234 and the trailing portion 236. The microthreads 246 have the same lead as the macrothread 238, the pitch being half the pitch of the macrothread 238. A cutting feature 248 is present at the microthreads in the leading portion 232 to make corresponding female microthreads in the bone tissue. In the illustrated embodiment, throughout the leading portion 232, transition portion 234 and trailing portion 236, the tops 250 of the microthreads 246 have the same radius of curvature as the radius of curvature a of the macrothreads 238. Also, the flank angles of the microthreads 246 correspond to those of the macrothreads 238. The effect of this conformation to the macrothreads 238 will now be explained.

The microthreads 246 are provided as two thread spirals, herein referred to as a first thread spiral 246a and a second thread spiral 246b. The first thread spiral 246a will follow the path of the macrothreads 238. The second thread spiral 246b will make its own path. The cutting feature 244 at the macrothread 238 creates a female thread profile in the bone having the same radius of curvature a and the flank angles γ as the macrothread 238. Thus, when the first thread spiral 246a of the microthreads 246 enters the female bone thread it can theoretically be in full contact with the bone, since the thread tops have the same radius of curvature a and the flanks have the same angles γ as the female bone thread. This means that the initial stability of the fixture can be higher than if the first thread spiral of the microthreads would not fill out the space of the female bone thread. It should be noted that while the cutting features 248 at the microthreads 246 will make a new path for the second thread spiral 246b, it will just adapt the inner areas of the already made female bone thread to conform with the inner areas of the first thread spiral 246a.

Figure 18:
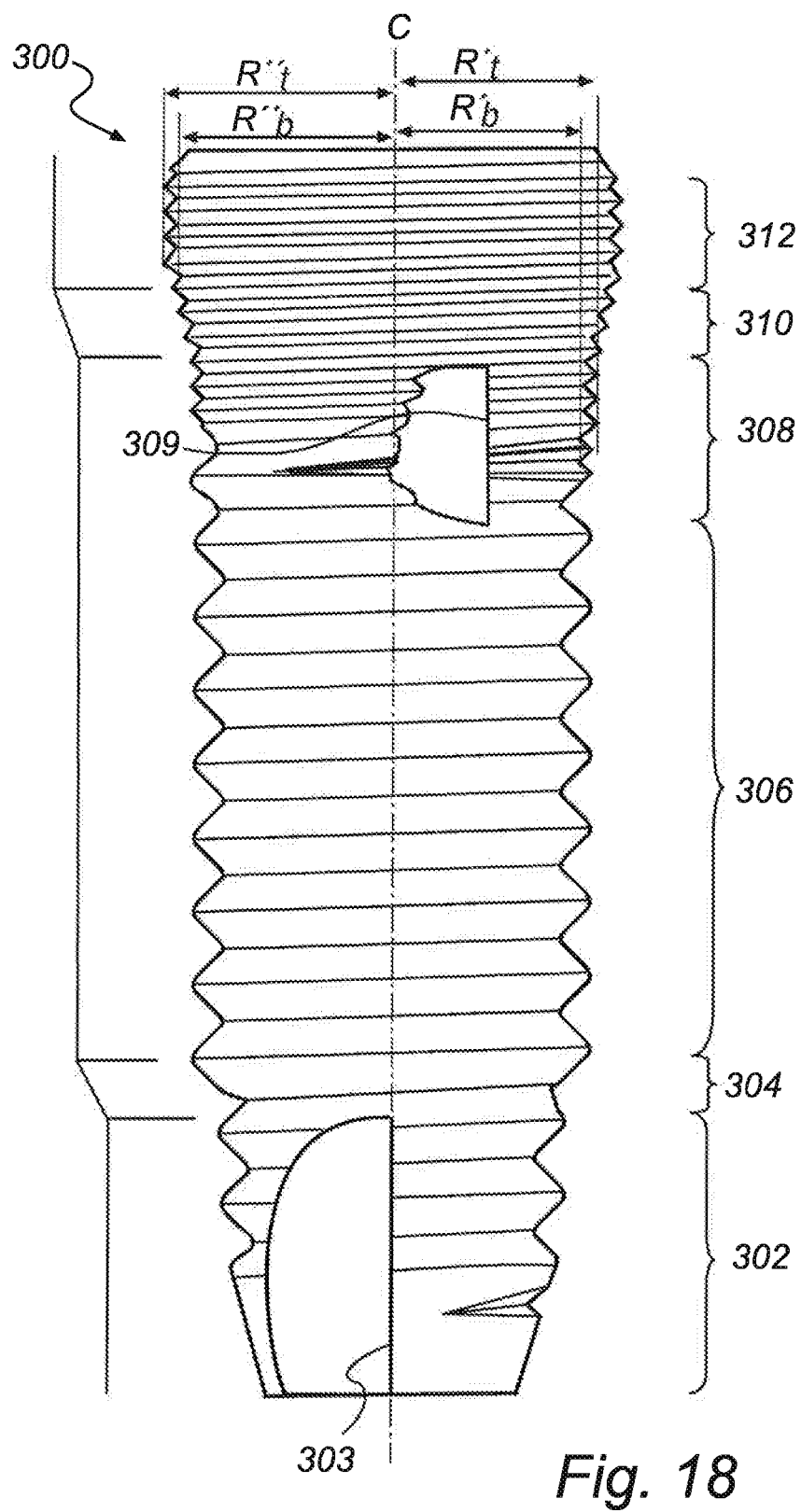
FIG. 18 illustrates a fixture according to at least another example embodiment of the invention.
Figure 19:
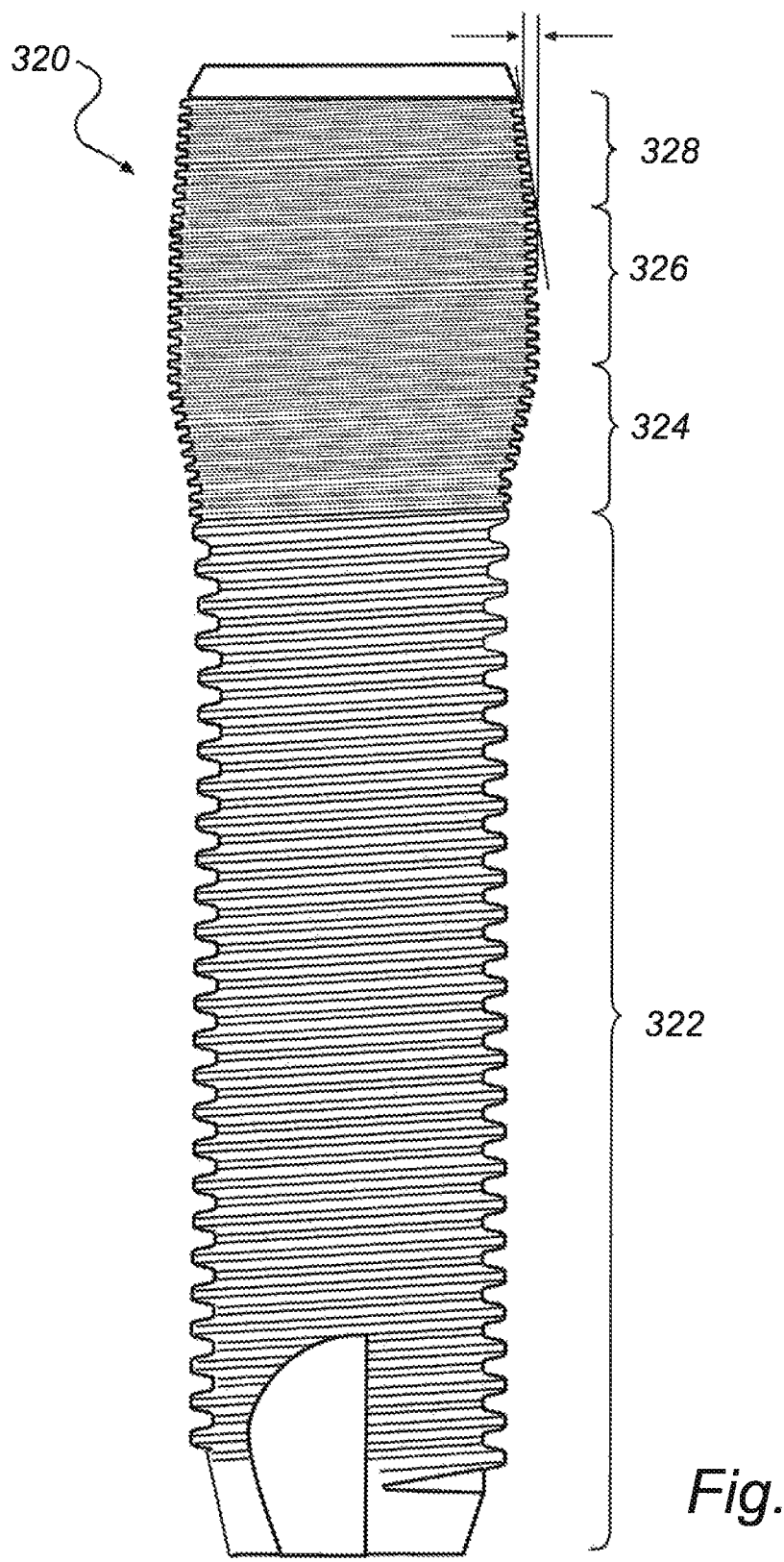
FIG. 19 illustrates a fixture according to at least yet another example embodiment of the invention.

It should be understood that the thread profiles shown in FIGS. 17a and 17b, having the same radius of curvature a and the same flank angles for the microthread tops and the macrothread tops, may also be applied to the previously illustrated embodiments, as well as in the subsequent embodiments of FIGS. 18 and 19. Thus, the various embodiments illustrated herein may be modified so that the tops of the microthreads and macrothreads have the same radius of curvature and the same flank angles.

FIG. 18 illustrates schematically a fixture 300 according to at least-another example embodiment of the invention. Similarly to the previously illustrated embodiments, the fixture 300 comprises a leading portion 302 having a cutting edge 303 for making a female thread in the bone. A transition portion 304 widens the fixture 300 towards a trailing portion 306 which will apply a pressure to the bone tissue, thus providing a tensile strain to the bone tissue. In the present fixture 300, said transition portion 304 is a first transition portion 304, and said trailing portion 306 is a first trailing portion 306. The first trailing portion 306 is after installation suitably located in the cancellous bone.

Coronally of the first trailing portion is a cutting portion 308. It is provided with a cutting edge 309 and has, similarly to the leading portion 302, the function of making a female bone thread in the bone. Since the first transition portion 304 has widened the fixture 300 relative to the leading portion 302, not only the first trailing portion 306 but also the cutting portion 308 is wider than the leading portion 302. However, while the wide first trailing portion 306 will apply a pressure to the bone tissue, the cutting portion 308 will with its cutting edge 309 cut away new bone substantially without applying any pressure to the bone tissue.

Coronally adjacent to the cutting portion 308, there is a second transition portion 310 further widening the fixture 300 to a larger diameter second trailing portion 312. The second trailing portion 312 will thus apply a tensile strain which is dependent on the increase in width achieved by the second transition portion 310. The second trailing portion 312 is after installation suitably located in the cortical bone. Thus, in order to provide a lower tensile strain to the cortical portion compared to the cancellous portion, the relative widening achieved by the second transition portion 310 may suitably be smaller than the relative widening achieved by the first transition portion 304.

In the cutting portion 308 the largest radial distance from the fixture axis C to a thread top of said cutting edge 309 is $R'_t$ and the largest radial distance from the fixture axis C to a thread bottom of said cutting edge is $R'_b$, wherein $R'_t \geq R_t$ and $R'_b \geq R_b$.

In the second trailing portion 312 the smallest radial distance from the fixture axis C to a thread top is $R''_t$ and the smallest radial distance from the fixture axis C to a thread bottom is $R''_b$.

Because the second trailing portion 312 should, suitably, apply a pressure to the cortical bone, at least one of the ratios $$\frac{R''_t - R'_t}{R'_t} \text{ and } \frac{R''_b - R'_b}{R'_b}$$

may be in the range of 0.01-0.1.

FIG. 19 illustrates a fixture 320 according to at least yet another example embodiment of the invention. Similarly, to the previously shown embodiments, the present fixture 320 comprises a leading portion 322, a transition portion 324 and a trailing portion 326. The trailing portion 326 is adapted to provide a tensile strain to the bone. Coronally adjacent to the trailing portion 326 the fixture 300 has a coronally tapering portion 328, which will provide relief for the coronal-most bone and allow it to flex back towards the fixture. Thus, this allows the tensile strain to be varied along the axial direction of the fixture. An alternative to a tapering portion 328, would be to have some other shape, e.g. cylindrical, the width of which is smaller than the width of the trailing portion 326.

In at least another embodiment, the fixture could be designed so that the trailing portion is adapted to provide a certain tensile strain to the cancellous bone, and then a narrower coronally following portion is present to provide a lower tensile strain to the cortical bone. It should be understood that anyone of the previously discussed and illustrated embodiments could be modified to present a narrower portion coronally of a trailing portion in order to provide a variation of strain in the axial extension of the fixture.

The various fixtures illustrated in the figures may be installed in different parts of the human bone tissue. However, according to at least some example embodiments the various fixtures illustrated in the figures are configured as dental fixtures to be inserted into jawbone.

The invention claimed is:

1. A fixture for insertion into a bore hole arranged in bone tissue, comprising
   a leading portion and a trailing portion, both of said portions comprising a respective outer surface being threaded for engagement with bone tissue,
   wherein thread tops and thread bottoms are provided alternatingly in the axial direction of the fixture,
   wherein the threading of the leading portion is provided with at least one cutting edge for making a female thread in the bone tissue,
   wherein in the leading portion the largest radial distance from the fixture axis to a thread top of said cutting edge is $r_t$ and the largest radial distance from the fixture axis to a thread bottom of said cutting edge is $r_b$,
   wherein in the trailing portion the smallest radial distance from the fixture axis to a thread top is $R_t$ and the smallest radial distance from the fixture axis to a thread bottom is $R_b$,
   the fixture comprising an intermediate transition portion having an apical end which borders to the leading portion and a coronal end which borders to the trailing portion, wherein the transition portion has an axial length L between its apical and coronal ends,
   wherein at least one of the ratios $$\frac{R_t - r_t}{r_t} \text{ and } \frac{R_b - r_b}{r_b}$$

is in the range of 0.01-0.3, and
   wherein any coronal widening of the trailing portion, with respect to the radial distance from the fixture axis to the thread tops and/or thread bottoms, is per axial unit length smaller than at least one of the ratios $$\frac{R_t - r_t}{L} \text{ and } \frac{R_b - r_b}{L}.$$

2. The fixture as claimed in claim 1, wherein at least one of the ratios $$\frac{R_t - r_t}{r_t} \text{ and } \frac{R_b - r_b}{r_b}$$

is in the range of 0.01-0.1.

3. The fixture as claimed in claim 2, wherein the axial length of the threading of the trailing portion is about 0.5-4 mm.

4. The fixture as claimed in claim 1, wherein at least one of the ratios $$\frac{R_t - r_t}{r_t} \text{ and } \frac{R_b - r_b}{r_b}$$

is in the range of 0.06-0.3.

5. The fixture as claimed in claim 4, wherein the axial length of the threading of the trailing portion is greater than 1 mm.

6. The fixture as claimed in claim 1, wherein in the trailing portion the largest radial distance from the fixture axis to a thread top is $R_{tl}$ and the largest radial distance from the fixture axis to a thread bottom is $R_{bl}$, wherein at least one of the ratios $$\frac{R_{tl} - r_t}{r_t} \text{ and } \frac{R_{bl} - r_b}{r_b}$$

is in the range of 0.01-0.3.

7. The fixture as in claim 1, wherein a geometrical tangent touches substantially all of the thread tops or substantially all of the thread bottoms in the trailing portion, wherein said tangent is parallel with the fixture axis.

8. The fixture as in claim 1, wherein the outer surface of the leading portion forms an angle of 177°-179°, such as 178° in relation to the outer surface of the transition portion.

9. The fixture as in claim 1, wherein the transition portion lacks cutting edges.

10. The fixture as in claim 1, wherein the threads in the trailing portion are microthreads.

11. The fixture as in claim 1, wherein at least a coronal portion of the transition portion is provided with microthreads which are continuous with microthreads in the trailing portion.

12. The fixture as in claim 1, wherein at least a coronal portion of the leading portion is provided with microthreads.

13. The fixture as in claim 1, wherein the axial length of the transition portion is about 0.5-4 mm.

14. The fixture as in claim 1, wherein the axial length of the transition portion is about 1-2 mm.

15. The fixture as in claim 1, wherein the threads in the trailing portion have substantially the same thread profile as the outermost part of the threads in the transition portion, the leading portion, or both.

16. The fixture as in claim 1, wherein the threads in the trailing portion, the transition portion and the leading portion have the same top radius, the same apical flank angle and the same coronal flank angle.

17. The fixture as in claim 1, wherein the thread height, the thread width, or both in the trailing portion is the same as or larger than in the leading portion.

18. The fixture as in claim 1, wherein said trailing portion is a first trailing portion and said transition portion is a first transition portion, the fixture further comprising a cutting portion, a second transition portion, and a second trailing portion, wherein the cutting portion has an apical end which borders to the first trailing portion and a coronal end which borders to the second transition portion, wherein the second transition portion has a coronal end which borders to the second trailing portion, wherein said cutting portion and said second trailing portion comprise a respective outer surface being threaded for engagement with bone tissue, wherein thread tops and thread bottoms are provided alternatingly in the axial direction of the fixture, wherein the threading of the cutting portion is provided with at least one cutting edge for making a female thread in the bone tissue, wherein in the cutting portion the largest radial distance from the fixture axis to a thread top of said cutting edge is $R'_t$ and the largest radial distance from the fixture axis to a thread bottom of said cutting edge is $R'_b$, wherein $R'_t \geq R_t$ and $R'_b \geq R_b$, wherein in the second trailing portion the smallest radial distance from the fixture axis to a thread top is $R''_t$ and the smallest radial distance from the fixture axis to a thread bottom is $R''_b$, and wherein at least one of the ratios $$\frac{R''_t - R'_t}{R'_t} \text{ and } \frac{R''_b - R'_b}{R'_b}$$

is in the range of 0.01-0.1.

19. The fixture as in claim 1, wherein said fixture is a dental fixture for arrangement in a jawbone.

20. The fixture as in claim 1, wherein the outer surface of the leading portion forms an angle a of less than 180° in relation to an outer surface of the transition portion, and wherein the outer surface of the transition portion forms an angle β of greater than 180° in relation to the outer surface of the trailing portion.

21. The fixture of claim 1, wherein the trailing portion, the intermediate portion or both include microthreads with at least one cutting edge for making a female thread in the bone tissue.

22. The fixture as in claim 1, wherein both the trailing portion and the intermediate portion include microthreads with at least one cutting edge for making a female thread in the bone tissue.

23. A method of inserting a fixture, into a bore hole arranged in bone tissue, comprising the steps of: making a female threading in a surface of the bone tissue defining the bore hole, wherein thread tops and thread bottoms are provided alternatingly in the axial direction of the bore hole, wherein the largest radial distance from the bore hole axis to a thread top is $r_t$ and the largest radial distance from the bore hole axis to a thread bottom is $r_b$, and inserting a threaded condensation portion of a fixture into the bore hole, such that at least one thread spiral follows in the path created by said female threading, wherein in said condensation portion the smallest radial distance from the fixture axis to a thread top is $R_t$ and the smallest radial distance from the fixture axis to a thread bottom is $R_b$, wherein at least one of the ratios $$\frac{R_t - r_t}{r_t} \text{ and } \frac{R_b - r_b}{r_b}$$

is in the range of 0.01-0.3.

24. A fixture set comprising, a fixture comprising a condensation portion, and a thread maker provided with at least one cutting edge and adapted to be rotated into a bore hole arranged in bone tissue for making a bone thread in the bone tissue prior to insertion of said fixture, the thread maker comprising a threaded outer surface, wherein thread tops and thread bottoms are provided alternatingly in the axial direction of the thread maker, wherein the largest radial distance from the thread maker axis to a thread top of said cutting edge is $r_t$ and the largest radial distance from the thread maker axis to a thread bottom of said cutting edge is $r_b$, wherein the fixture comprises an outer surface being threaded for engagement with bone tissue, wherein thread tops and thread bottoms are provided alternatingly in the axial direction of the fixture, wherein the smallest radial distance from the fixture axis to a thread top of said condensation portion is $R_t$ and the smallest radial distance from the fixture axis to a thread bottom of said condensation portion is $R_b$, wherein at least one of the ratios $$\frac{R_t - r_t}{r_t} \text{ and } \frac{R_b - r_b}{r_b}$$

is in the range of 0.01-0.3.

25. The fixture set as in claim 24, wherein the fixture is a fixture for insertion into a bore hole arranged in bone tissue, comprising a leading portion and a trailing portion, both of said portions comprising a respective outer surface being threaded for engagement with bone tissue, wherein thread tops and thread bottoms are provided alternatingly in the axial direction of the fixture, wherein the threading of the leading portion is provided with at least one cutting edge for making a female thread in the bone tissue, wherein in the leading portion the largest radial distance from the fixture axis to a thread top of said cutting edge is $r_t$ and the largest radial distance from the fixture axis to a thread bottom of said cutting edge is $r_b$, wherein in the trailing portion the smallest radial distance from the fixture axis to a thread top is $R_t$ and the smallest radial distance from the fixture axis to a thread bottom is $R_b$, the fixture comprising an intermediate transition portion having an apical end which borders to the leading portion and a coronal end which borders to the trailing portion, wherein the transition portion has an axial length L between its apical and coronal ends, wherein at least one of the ratios $$\frac{R_t - r_t}{r_t} \text{ and } \frac{R_b - r_b}{r_b}$$

is in the range of 0.01-0.3, and wherein any coronal widening of the trailing portion, with respect to the radial distance from the fixture axis to the thread tops and/or thread bottoms, is per axial unit length smaller than at least one of the ratios $$\frac{R_t - r_t}{L} \text{ and } \frac{R_b - r_b}{L}.$$

* * * * *